US011031119B2

(12) United States Patent
Ricci et al.

(10) Patent No.: US 11,031,119 B2
(45) Date of Patent: *Jun. 8, 2021

(54) DENTAL IMAGES PROCESSED WITH DEEP LEARNING FOR NATIONAL SECURITY

(71) Applicants: Richard Ricci, New York, NY (US); Andrea Cambria, New York, NY (US)

(72) Inventors: Richard Ricci, New York, NY (US); Andrea Cambria, New York, NY (US)

(73) Assignee: Cube Click, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/920,043

(22) Filed: Jul. 2, 2020

(65) Prior Publication Data
US 2021/0142885 A1    May 13, 2021

Related U.S. Application Data

(63) Continuation-in-part of application No. 16/683,116, filed on Nov. 13, 2019, now Pat. No. 10,748,650.

(51) Int. Cl.
*G16H 30/20* (2018.01)
*G06Q 30/06* (2012.01)
(Continued)

(52) U.S. Cl.
CPC .......... *G16H 30/20* (2018.01); *G06F 16/55* (2019.01); *G06N 3/08* (2013.01); *G06Q 30/0601* (2013.01)

(58) Field of Classification Search
None
See application file for complete search history.

(56) References Cited

U.S. PATENT DOCUMENTS 9,898,659 B2 *  2/2018  Kanagasingam ......... G06T 7/10
9,995,695 B2 *  6/2018  Schulte ..................... A61B 6/14
(Continued)

FOREIGN PATENT DOCUMENTS

WO    WO-2004057034 A1 *  7/2004  ........... C12Q 1/6883

OTHER PUBLICATIONS

Loos, Bruno G., Raymond P. John, and Marja L. Laine. "Identification of genetic risk factors for periodontitis and possible mechanisms of action." Journal of clinical periodontology 32 (2005): 159-179. (Year: 2005).*

*Primary Examiner* — Michelle M Entezari

(57) ABSTRACT

Deep learning of dental images for national security is described. A computer may receive dental images of a patient from a dental provider. The computer is configured to match dental images to law enforcement databases such as a terrorist database. The process begins with matching a dental image to an anatomy probability dataset and a pathology probability dataset, then correlating it with a patient database to identify a person of interest. With different resolutions each neural network deep learns to probability map and detect different dental object probabilities to authenticate an individual. Further, the dental images will be associated with GPS coordinates to track movements of an individual. The datasets will be provided to e-commerce providers, e-commerce consumers, e-commerce administrators, machine learning entities, government entities and law enforcement entities which may exchange or transfer the data over a communication network such as the internet to locate a person of interest.

20 Claims, 15 Drawing Sheets

(51) Int. Cl.
*G06F 16/55* (2019.01)
*G06N 3/08* (2006.01)

(56) References Cited

U.S. PATENT DOCUMENTS

| | | | | |
|---|---|---|---|---|
| 10,572,625 | B2* | 2/2020 | Golay | G16H 30/20 |
| 2003/0165851 | A1* | 9/2003 | Edinger | C07K 14/47 |
| | | | | 435/6.14 |
| 2003/0198970 | A1* | 10/2003 | Roberts | C07K 16/18 |
| | | | | 435/6.14 |
| 2007/0183633 | A1* | 8/2007 | Hoffmann | G06K 9/00221 |
| | | | | 382/116 |
| 2008/0033754 | A1* | 2/2008 | Smith | G16H 10/60 |
| | | | | 705/2 |
| 2010/0022846 | A1* | 1/2010 | Pouletty | G06T 7/0012 |
| | | | | 600/300 |
| 2014/0087342 | A1* | 3/2014 | Campanatti, Jr. | G09B 23/28 |
| | | | | 434/262 |
| 2016/0166220 | A1* | 6/2016 | Bar-Shalev | A61B 6/032 |
| | | | | 600/427 |
| 2017/0007148 | A1* | 1/2017 | Kaditz | A61B 5/055 |
| 2017/0199189 | A1* | 7/2017 | Wade | G16H 50/30 |
| 2017/0199193 | A1* | 7/2017 | Filvaroff | G01N 33/57426 |
| 2019/0262399 | A1* | 8/2019 | Wang | C12Q 1/6851 |
| 2020/0066391 | A1* | 2/2020 | Sachdeva | A61C 5/30 |
| 2020/0105413 | A1* | 4/2020 | Vladimirova | G16H 20/30 |

\* cited by examiner

DENTAL IMAGES PROCESSED WITH DEEP LEARNING FOR NATIONAL SECURITY

CLAIM OF PRIORITY

This application claims priority to U.S. Application 62/875,319 filed Jul. 17, 2019, the contents of which are herein fully incorporated by reference in its entirety.

FIELD OF THE EMBODIMENTS

The field of the embodiments relate to a system to provide at least one of: deep learning, machine learning of dental images for national security utilizing e-commerce. The dental image of at least one of: an e-commerce consumer, a person of interest may be processed by at least one of: a machine learning mechanism, a deep learning mechanism to learn the following:

(1) At least one of: deep learn, machine learn to train a microprocessor to process at least one of: a first, second, a multiple dental image with a deep neural network.
(2) At least one of: deep learn, machine learn to match and identify dental image landmark probabilities of a dental image.
(3) At least one of: deep learn, machine learn to match and identify image class landmark probabilities of a dental image.
(4) At least one of: deep learn, machine learn to match and identify object class landmark probabilities of a dental image.
(5) At least one of: deep learn, machine learn to match and identify spatial landmark probability relationships of a dental image.
(6) At least one of: deep learn, machine learn to match and identify object probability landmarks of dental image.
(7) At least one of: deep learn, machine learn to match and identify object probability relationships of a dental image.
(8) At least one of: deep learn, machine learn to generate landmark probability maps of a dental image.
(9) At least one of: deep learn, machine learn to match and identify landmark probability maps of a dental image.
(10) At least one of: deep learn, machine learn to match and identify object class probabilities and image class probabilities of a dental image.
(11) Correlate at least one of: a deep learned, a machine learned dental image data to a dental image dataset and merge with an e-commerce consumer dataset to produce an e-commerce dataset.
(12) At least one of: deep learn, machine learn to generate at least one of: a probability diagnosis, a probability demonstration aid from the e-commerce dataset.
(13) At least one of: deep learn, machine learn to provide to at least one of: an e-commerce dataset, a person of interest dataset to at least one of: an e-commerce provider, an e-commerce consumer, an e-commerce administrator, a machine learning entity, an e-commerce organization, a government entity, a law enforcement entity, a person of interest.
(14) At least one of: deep learn, machine learn to process a transaction of least one of: an exchange, a transfer, a buy, a sell with at least one of: a dental image, an e-commerce consumer dental image, a dental image dataset, an e-commerce consumer dataset, an e-commerce dataset, a person of interest dataset over a communication network, wherein a communication network includes at least one of: a secure communication network, an encrypted communication network, the internet, an intranet, an extranet, an internet, an internet transaction service, an online transaction service, a mobile network, a wireless network, an online transaction processing (OLTP) service, an online analytical processing (OLAP) service, a transaction platform.

BACKGROUND OF THE EMBODIMENTS

Digital dental images have revolutionized the entire dental field. Today, digital radiography is common place in the vast majority of dental offices. Doctors, hygienists and staff are ubiquitously trained in the taking of digital dental images. Digital dental images have led to huge improvements in patient diagnosis and treatment options. Digital dental x-rays are processed vastly faster than traditional film dental x-rays. In addition to this, the patient's radiation exposure is significantly less with digital dental x-rays. Patient dental image management service(s) provide a wide variety of applications ranging from offsite image hosting, dental image attachments to insurance claims, dental laboratory scans, x-ray to graphic based charting and dental charting by voice command.

In 2014 52.3% of Americans reported visiting the dentist every 6 months. Statistically, everyone will need to have routine or emergency dental care in their lifetime. It is highly likely that each of these patients will require dental x-rays. Dental images, such as dental x-rays and digital dental images, offer a unique authentication of an individual and can be immensely useful for law enforcement to track and identify patients who may be persons of interest. Hence there is a need to develop this technology for national security purposes.

SUMMARY OF THE EMBODIMENTS

The present invention and its embodiments relate to at least one of: deep learning, machine learning of dental images for national security utilizing e-commerce. Wherein e-commerce is the activity of transferring at least one of: a product, a good, a data, a currency, a discount, a software, an application, an advertisement, an image, an information, a service over a communication network. Wherein, a communication network is at least one of: a secure communication network, an encrypted communication network, the internet, an intranet, an extranet, an internet, an internet transaction service, an online transaction service, a mobile network, a wireless network, an online transaction processing (OLTP) service, an online analytical processing (OLAP), a transaction platform, an internet transaction platform. Wherein, national security is the security and defense of a nation state, including its citizens, economy, and institutions, which is regarded as a duty of government. The system may provide at least one of: deep learning, machine learning of a dental image for national security utilizing e-commerce. The system may include a microprocessor device. The microprocessor is configured to execute an instruction in any order. Further, the microprocessor is configured to omit an instruction in any order. Wherein an instruction is at least one of: a process, a match, an identify, a generate, a train, a provide, a transaction, an exchange, transfer, a buy, a sell. The microprocessor may be configured to receive dental images of at least one of: an e-commerce consumer, a person of interest from at least one of: an e-commerce provider, an e-commerce administrator, a machine learning entity, an e-commerce organization, a government entity, a law enforcement entity, a person of interest. The microprocessor may be configured to process dental images of at least one of: an e-commerce consumer, a person of interest from at least one of: an e-commerce provider, an e-commerce administrator, a machine learning entity, an e-commerce organization, a government entity, a law enforcement entity, a person of interest. An e-commerce consumer may be a person of interest. An example of a dental image e-commerce provider may include at least one of: a business entity, a business owner, an employer, a wholesaler, a retailer, a professional, a dentist, a dental hygienist, a dental professional, a physician, a health professional, a group, a veterinarian, a veterinarian professional, a research entity, a law enforcement entity, a public administration entity, a bioinformatics service, an insurance company, a cloud based storage service. Further, an e-commerce provider may be an expert in one or more of the following fields of dentistry: restorative, prosthodontics, periodontics, endodontics, oral surgery, pediodontics, radiology, pathology, tempro-mandibular joint (TMJ) specialist, orthodontist. An example of a dental image e-commerce consumer may include at least one of: a patient, an individual, a person of interest, a guardian, a group, an employee. An example of an e-commerce administrator may include at least one of: an administrator, an administrator entity, a law enforcement agency, a governing agency. An example of a person of interest may be at least one of: a terrorist, a violent criminal, a nonviolent criminal, a cybercrime criminal, a political criminal, a white collar criminal, an innocent person. Wherein, a terrorist may be at least one of: a terrorist, an assassin, an arms trader, a piracy, a smuggler, an arsonist, a hijacker. Wherein, a violent crime may include at least one of: a homicide, a kidnapper, a rapist, a sex assault, a sexual offender, a child sex offender, an arsonist, a domestic violence, a sex trafficker, a fugitive, a drug trafficker, an abducted child, a hate crime, a violent crime. Wherein, a nonviolent crime may be at least one of: a theft, a property crime, a racketeering crime, a gambling crime, a bribery crime, a prostitution crime, a missing person, a discrimination crime, a traffic crime, a failure to pay a child support, a failure to pay an alimony payment, a shoplifting, a non violent crime. Wherein, a cybercriminal may include at least one of: a cyberterrorist, a cyberwarefare, a cyberextortion, a cyber sex trafficking, an espionage, a ransomware, a malware, a data hacker, an identity theft, a computer crime. Wherein, a political crime may include at least one of: a treason, a sedition, a terrorism, an espionage, a religious crimes, an anti-Semite crime, a crime against a government. Wherein, a white collar crime may include at least one of: an insider trader, a ponzi scheme, an embezzler, an extortionist, a forgery, a nepotism, a tax evader, a briber, a fraud, a counterfeiter, a money laundering, a copyright infringement, a non violent crime.

Next, the dental images for e-commerce may be processed with at least one of: deep learning, machine learning with a computer vision image class dataset and may further be processed with a large computer vision image class dataset. A computer vision image class may be matched to at least one of: an individual e-commerce consumer dataset, a larger e-commerce dataset. Both computer vision datasets and the e-commerce datasets may be merged and correlated with large datasets and provided to at least one of: an e-commerce provider, an e-commerce consumer, an e-commerce administrator, a machine learning entity, an e-commerce organization, a government entity, a law enforcement entity, a person of interest. The dental images for e-commerce may also be processed with at least one of: a deep learning computer vision object class dataset, a machine learning computer vision object class dataset. A computer vision object class from the deep learned and/or machine learned computer vision object class dataset may be matched to at least one of: an individual e-commerce consumer dataset, a larger e-commerce dataset. Both computer vision datasets and the e-commerce consumer dataset may be merged and correlated with large datasets and provided to at least one of: an e-commerce provider, an e-commerce consumer, an e-commerce administrator, a machine learning entity, an e-commerce organization, a government entity, a law enforcement entity, a person of interest. In addition, a cluster analysis of the e-commerce consumer dataset may be performed with a cluster dataset to produce correlated dental images for e-commerce. Furthermore, the correlated dental images for e-commerce may be provided to a machine learning entity to compile a diagnostic probability aid for at least one of: an e-commerce provider, an e-commerce consumer, an e-commerce administrator, a machine learning entity, an e-commerce organization, a government entity, a law enforcement entity, a person of interest.

In another embodiment of the present invention, a microprocessor for providing at least one of: deep learning, machine learning of dental images for national security utilizing e-commerce is described. The microprocessor may include a computer vision component configured to analyze the dental images for e-commerce, a memory configured to store instructions associated with at least one of: an aggregator, a processing service, and a microprocessor coupled to the computer vision component and the memory. The microprocessor may execute the instructions associated with an aggregator. The aggregator may include an image processing engine. The image processing engine may be configured to receive a dental image of an e-commerce consumer from an e-commerce provider. Another example of an e-commerce provider may include a business. Another example of an e-commerce consumer may be a consumer. Another example of an e-commerce administrator may include an administrator. E-commerce providers, e-commerce consumers and e-commerce administrators may process, exchange, transfer and share e-commerce consumer dental images and e-commerce datasets between at least one of: business to business (B2B), business to consumer (B2C), consumer to business (C2B), consumer to consumer (C2C), business to administration (B2A), consumer to administration (C2A). Further e-commerce providers, e-commerce consumers and e-commerce administrators may use at least of: deep learning, machine learning of a dental image correlated with an e-commerce dataset to least one of: an exchange, a transfer, buy, sell at least one of: a product, a good, a data, an image, an information, a service over a communication network. Wherein a communication network is at least one of: a secure communication network, an encrypted communication network, the internet, an intranet, an extranet, an internet, an internet transaction service, an online transaction service, a mobile network, a wireless network, an online transaction processing (OLTP) service, online analytical processing (OLAP) service, a transaction platform to at least one of: an e-commerce provider, an e-commerce consumer, an e-commerce administrator, a machine learning entity, an e-commerce organization, a national security organization, a judiciary agency, a military agency, a government agency, a government, a law enforcement agency. Wherein, a national security organization may include at least one of: National Security Agency (NSA), Central Intelligence Agency (CIA), Federal Bureau of Investigation, Defense Intelligence Agency (DIA), Homeland Security, a government security agency. Wherein a judiciary agency may include at least one of: The Department of Justice (DOJ), The Supreme Court of the United Sates, a general federal trial court, a Count of International Trade, a Foreign Intelligence Surveillance Court, an Alien Terrorist Removal Court, a federal appellate court, a Court of Appeals for the Armed Forces, an immigration court, a State supreme court, a Court of Appeals, appellate court, a civil court, a criminal court, a family court, a surrogate's court, a court. Wherein, a military agency may include at least one of: The Army, The Marines, The Navy, The Air Force, The National Guard, Military Police, The Coast Guard, The National Guard, a military agency. Wherein, at least one of: a government agency, a government may include at least one of: The Executive Office of the President, The United States Senate, The United States House of Representatives, a governing body, a governing agency. Wherein, a law enforcement agency may include at least one of: a police department, a sheriff office, a state police force, The United States Park Police, Child Protective Services (CPS), National Center for Missing & Exploited Children (NCMEC), a law enforcement agency.

The types of goods and services may be one or more of: a tangible good, a physical good (a product), an intangible product, a digital good, a service. At least one of: e-commerce providers, e-commerce consumers, e-commerce administrators, a machine learning entity, an e-commerce organization, a government entity, a law enforcement entity may at least one of: an exchange, a transfer, a buy, a sell at least one of: a dental image, a dental image dataset, an e-commerce dataset, a dataset of at least one of: a tangible good, a physical good (a product), an intangible product, a digital good, a service. Further, the e-commerce providers, e-commerce consumers, e-commerce administrators, machine learning entities, e-commerce organization, government entities, law enforcement entities, persons of interest may at least one of: an exchange, a transfer, a buy, a sell over a communication network at least one of: e-commerce consumer dental image landmark probabilities, image class landmark probabilities, object class landmark probabilities, spatial landmark probability relationships, object probability landmarks, object probability relationships, dental image landmark probability maps.

The dental images for e-commerce may next be processed with at least one of: a deep learning, a machine learning object class dataset. An object class from at least one of: a deep learned object class, a machine learned object class dataset may be matched and identified to the dental images for e-commerce. The dental images for e-commerce may be processed with at least one of: a deep learning, a machine learning to at least one of: an image class, an object class, a deep neural network, a convolutional neural network, dental image landmark probabilities, image class landmark probabilities, object class landmark probabilities, spatial landmark probability relationships, object probability landmarks, object probability relationships to generate at least one of: dental image landmark probability maps, image class probabilities, object class probabilities, an image confidence score, an object confidence score and e-commerce datasets.

An image class, object class and a landmark probability map of dental images may be matched and identified to the dental images of at least one of: an e-commerce consumer, a person of interest. In addition, an e-commerce consumer dataset of an e-commerce consumer associated with the dental images for e-commerce may be queried and received from an e-commerce provider. Subsequently the dental images for e-commerce, the image class, the object class, and the landmark probability map may be inserted to an e-commerce dataset. Furthermore, a cluster analysis of an e-commerce consumer dataset's personal information may be processed with a cluster dataset to produce correlated dental images for a correlation dataset. Moreover, the correlation dataset may be provided to a machine learning entity to compile at least one of: a diagnostic probability aid, a probability demonstration aid for at least one of: an e-commerce provider, an e-commerce consumer, an e-commerce administrator, a machine learning entity, an e-commerce organization, a government entity, a law enforcement entity, a person of interest.

In yet another embodiment of the present invention, a method of providing deep learning and/or machine learning of dental images for national security utilizing e-commerce is described. The method may include receiving dental images of an e-commerce consumer or a person of interest from an e-commerce provider. An example of a dental image e-commerce provider may include at least one of: a business entity, a business owner, an employer, a wholesaler, a retailer, a professional, a dentist, a dental hygienist, a dental professional, a physician, a health professional, a group, a veterinarian, a veterinarian professional, a research entity, a law enforcement entity, a public administration entity, a bioinformatics service, an insurance company, a cloud based storage service. An example of a dental image e-commerce consumer includes a patient, an individual, a person of interest, a guardian, a group, a person of interest, an employee. An example of an e-commerce administrator includes an administrator, an administrator entity and a governing agency. An example of a dental image may include an electronically captured dental image, a scanned dental image, an archived dental image.

The dental images for e-commerce may next be processed with at least one of: a deep learning image class dataset, a machine learning image class dataset. An image class from a deep learned image class dataset and/or a machine learned image class dataset may be matched to the dental images for e-commerce. The dental images for e-commerce may also be processed with at least one of: a deep learning object class, a machine learning object class and a dental image landmark probability map dataset. An object class and a dental image landmark probability map dataset may be matched to the dental images for e-commerce. In addition, an e-commerce consumer dataset of an e-commerce consumer associated with the dental images for e-commerce may be queried and received from an e-commerce organization. Subsequently, the dental images from at least one of: a dental image for e-commerce, an image class, an object class, dental image landmark probability map may be inserted into the e-commerce consumer dataset. Furthermore, a cluster analysis of the e-commerce consumer dataset may be performed with a cluster dataset to produce correlated dental images for e-commerce. Moreover, the correlated dental images for e-commerce may be provided to a machine learning entity to compile a diagnostic probability aid for at least one of: an e-commerce provider, an e-commerce consumer, an e-commerce administrator, a machine learning entity, an e-commerce organization, a government entity, a law enforcement entity, a person of interest.

An e-commerce consumer may include at least one of: a patient, an individual, a guardian, a group, an employee, a person of interest and may process a transaction of at least one of: an exchange, a transfer, a buy, a sell of at least one of: a dental image, a dataset with at least one of: an e-commerce provider, an e-commerce consumer, an e-commerce administrator, a machine learning entity, an e-commerce organization, a government entity, a law enforcement entity, a person of interest in exchange for at least one of: a currency, a data, a discount, a product, a good, a software, an application, an advertisement. An e-commerce consumer may retain at least one of: their dental images, their datasets on their client device that may include at least one of: a server, a dental office server, a network node, a desktop computer, a workstation, a laptop computer, a cell phone, a tablet, a mobile device, an augmented reality display, virtual reality display, among others. A least one of: a microprocessor, an aggregator, a processor, a processing device may be configured to omit a specific client device depending on at least one of: e-commerce consumer, an e-commerce provider, an e-commerce administrator, a machine learning entity, an e-commerce organization, a government entity, a law enforcement entity, a person of interest request(s). Further, if authorization is given from an e-commerce consumer, at least one of: an e-commerce provider, an e-commerce administrator, a machine learning entity, an e-commerce organization, a government entity, a law enforcement entity, a person of interest may exchange, transfer, buy, sell at least one of: an e-commerce consumer dental image, a dataset with at least one of: an e-commerce provider, an e-commerce consumer, an e-commerce administrator, a machine learning entity, an e-commerce organization, a government entity, a law enforcement entity, a person of interest for at least one of: a currency, a data, a discount, a product, a good, a software, an application, an advertisement.

It is an object of the embodiments of the present invention to provide at least one of: deep learning, machine learning of a dental image for national security utilizing e-commerce.

It is an object of the embodiments of the present invention to at least one of: deep learn, machine learn to determine an image class, an object class, dental image landmark probabilities, image class landmark probabilities, object class landmark probabilities, spatial landmark probability relationships, object probability landmarks, object probability relationships, dental image landmark probability map of a dental image.

It is an object of the embodiments of the present invention to at least one of: deep learn, machine learn to correlate dental images with an e-commerce dataset(s) and perform a cluster analysis to produce correlated dataset(s).

It is an object of the embodiments of the present invention to provide the correlated dental images for e-commerce to a machine learning entity to compile a diagnostic probability aid and probability demonstration aid for at least one of: an e-commerce provider, an e-commerce consumer, an e-commerce administrator, a machine learning entity, an e-commerce organization, a government entity, a law enforcement entity, a person of interest.

It is the object of the embodiment of the present invention to correlate a dental image landmark probability map with an e-commerce dataset and provide the correlated information to an e-commerce provider, an e-commerce consumer, an e-commerce administrator, a machine learning entity, an e-commerce organization, a government entity, a law enforcement entity, a person of interest to at least one of: buy, sell, transfer, exchange the correlated information over a communication network such as at least one of: a secure communication network, an encrypted communication network, the internet, an intranet, an extranet, an internet, an internet transaction service, an online transaction service, a cell phone, a mobile network, a wireless network, an online transaction processing (OLTP) service, an online analytical processing (OLAP) service, a transaction platform.

These and other features, aspects and advantages of the present invention will become better understood with reference to the following drawings, description and claims.

DESCRIPTION OF THE PREFERRED EMBODIMENTS

Figure 1:
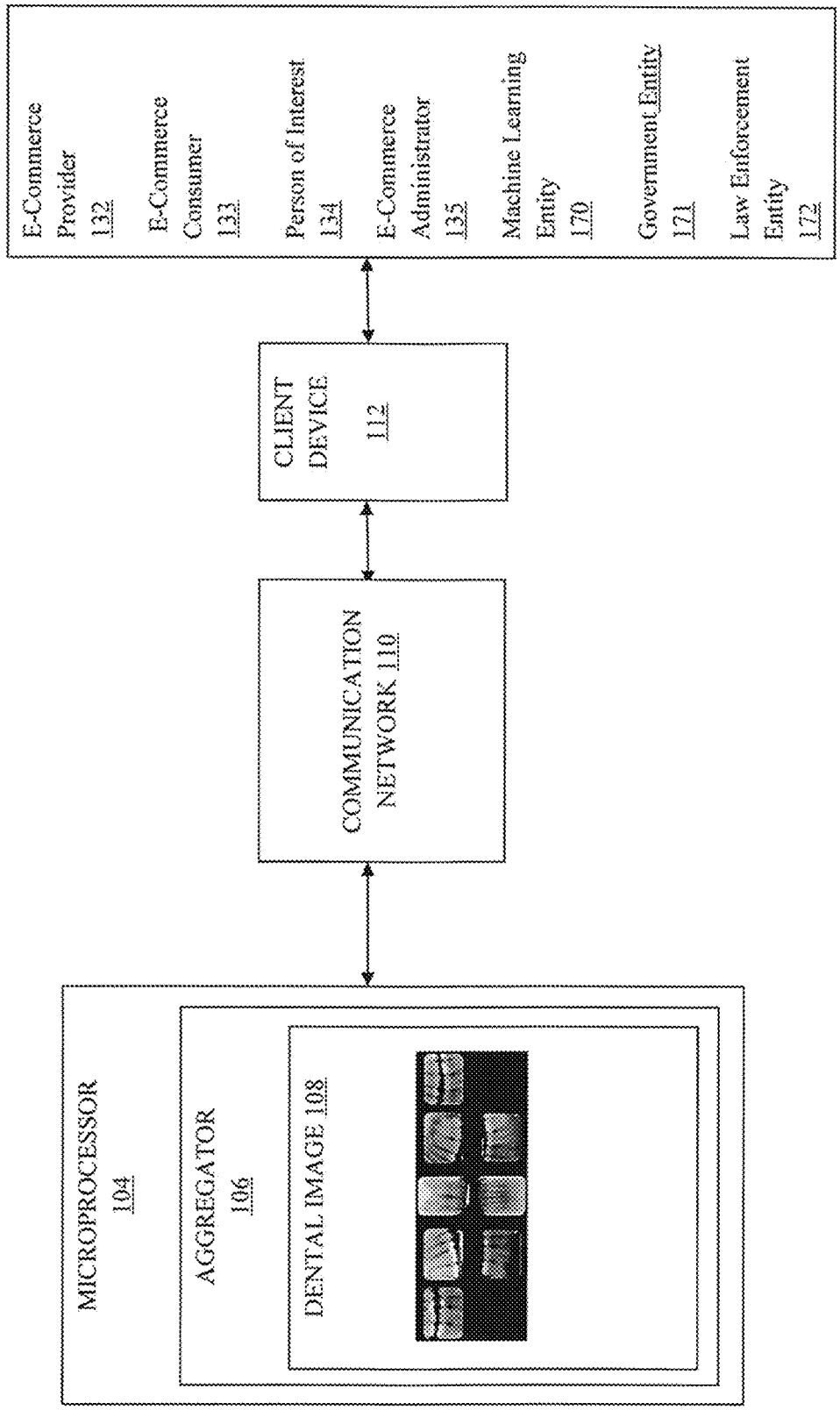
FIG. 1 shows a conceptual diagram illustrating examples of providing at least one of: deep learning, machine learning of dental images for national security utilizing e-commerce, according to an embodiment of the invention.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations may be made thereto.

FIG. 1 shows a conceptual diagram illustrating examples of at least one of: deep learning, machine learning of dental images for national security utilizing e-commerce. Wherein e-commerce is the activity of at least one of: buying, selling, transferring, exchanging of at least one of: a product, a good, a data, an image, an information, a services over a communication network such as the internet. In an example scenario, a microprocessor 104 may execute (or provide) an aggregator 106. The microprocessor 104 may include at least one of: a physical server providing service(s), application(s), an interface to client devices 112. A service (such as an aggregator 106) may include an application performing operations in relation to a client application and/or a subscriber, among others. The microprocessor is configured to execute an instruction in any order and is also configured to omit an instruction in any order. Wherein an instruction is at least one of: a process, a match, an identify, a generate, a train, a provide, a transaction, an exchange, transfer, a buy, a sell. Further, the microprocessor 104 may include at least one of: part of a workstation, a data warehouse, a data center, a cloud based distributed computing source, a processing device, a processor.

In an example scenario, the microprocessor 104 may execute an aggregator 106. The aggregator 106 may receive a dental image 108 of at least one of: an e-commerce consumer, a person of interest 134 from an e-commerce provider 132. The dental images 108 of at least one of: an e-commerce consumer 133, a person of interest 134 may be obtained by at least one of: a digital x-ray, an x-ray, a digital image, an image, a cell phone captured image, a photographic image, a toothbrush with an imaging device, a toothbrush with an imaging device being a camera, a film based x-ray, a digitally scanned x-ray, a digitally captured x-ray, a scintillator technology based image, a trans-illumination image, a fluorescence technology based image, a blue fluorescence technology based image, a laser based technology based image, a magnetic resonance image (MRI), a cone beam computed tomography (CBCT), a computed tomography (CT) scan based image of a section and/or an entirety of a mouth, an image obtained from a wavelength between 1 picometer and 100000 kilometers, a gamma ray based technology, an ultraviolet based technology, a visible light based technology, an infrared based technology, a high frequency based technology, a microwave based technology, a low frequency based technology, a radio wave based technology and all future embodiments.

The dental image e-commerce provider 132 may utilize at least one of: an image capture device, a data storage device. The image capture device may include at least one of: an x-ray equipment, a digital camera, a cell phone camera, an indirect or direct flat panel detector (FPD), a charged couple device (CCD), a phosphor plate radiography device, a picture archiving and communication system (PACS), a photo-stimulable phosphor (PSP) device, a computer tomography (CT) device, a wireless complementary metal-oxide-semiconductor (CMOS), a cone beam computed tomography (CBCT) device, an imaging device, all future embodiments.

Next, the dental images 108 of at least one of: an e-commerce consumer 133, a person of interest 134 may be processed with at least one of: a deep learning, a machine learning to an image class dataset. The deep learning and/or machine learned image class dataset may include a number of dental images of at least one of: an e-commerce consumer 133, a person of interest 134 from an e-commerce provider 132 with annotations associated with image class structures. An image class may be matched to the dental images 108 of at least one of: an e-commerce consumer 133, a person of interest 134. Furthermore, the dental images 108 of at least one of: an e-commerce consumer 133, a person of interest 134 may also be processed and matched with deep learning and/or a machine learned dental object classification dataset and a landmark probability map dataset.

Subsequently, the dental images 108, the image class, the object class, and a landmark probability map may be inserted to an e-commerce dataset associated with at least one of: an e-commerce consumer 133, a person of interest 134. An e-commerce dataset may include attributes and other information associated with an e-commerce consumer. In addition, a cluster analysis of an e-commerce dataset may be performed with a cluster dataset to produce correlated dental images for a correlation dataset. The cluster dataset may include annotated information associated with a population and dental classifications associated with the population. Furthermore, the correlated dental images for e-commerce may be provided to a machine learning entity 170 to compile a diagnostic probability aid for at least one of: an e-commerce provider 132, an e-commerce consumer 133, an e-commerce administrator 135, a machine learning entity, an e-commerce organization 169, a government entity, a law enforcement entity, a person of interest 134.

An example of a dental image e-commerce consumer 133 includes at least one of: a patient, an individual, a guardian, a group, a person of interest 134, an employee. The e-commerce provider 132 may include a business, a business entity, a business owner, an employer, a wholesaler, a retailer, a professional, a dentist, a dental hygienist, a dental professional, a physician, a health professional, a group, a veterinarian, a research entity, a law enforcement entity, a public administration entity, a bioinformatics service, an insurance company, and a cloud based storage service among others. An example of an e-commerce administrator includes an administrator, an administrator entity, a governing agency, a government. An example of a government entity includes a government, legislative body, a country, a sovereign nation. An example of a law enforcement entity includes a department of justice, a court, a police department, a correctional facility.

The dental images 108 of at least one of: an e-commerce consumer, a person of interest 134, an e-commerce dataset, the correlated dental images of an e-commerce dataset may be provided to an e-commerce provider 132, e-commerce consumer 133, e-commerce administrator 135, a machine learning entity 170, an e-commerce organization 169, a government entity, a law enforcement entity, a person of interest through a client device 112. An example of the client device 112 may include at least one of: a server, a dental office server, a network node, a desktop computer, a workstation, a laptop computer, a cell phone, a tablet, a mobile device, an augmented reality display, virtual reality display, among others. A least one of: a microprocessor, an aggregator, an processor, a processing device may be configured to omit a specific client device depending on at least one of: e-commerce consumer, an e-commerce provider, an e-commerce administrator, a machine learning entity, an e-commerce organization, a government entity, a law enforcement entity, a person of interest request(s).

The e-commerce provider 132, e-commerce consumer 133, e-commerce administrator 135, a machine learning entity 170, an e-commerce organization 169, a government entity, a law enforcement entity, a person of interest 134 may be provided with at least one of: an e-commerce dataset, the correlated dental images of an e-commerce consumer for a diagnostic probability aid. An integrated diagnostic probability aid of at least one of: an e-commerce consumer 133, a person of interest 134, an annotated information dataset associated with the dental images for at least one of: an e-commerce consumer 133, a person of interest 134 may be provided to at least one of: an e-commerce provider 132, e-commerce consumer 133, e-commerce administrator 135, a machine learning entity 170, e-commerce organization 169, a government entity, a law enforcement entity, a person of interest 134.

The microprocessor 104 may communicate with the client device 112 through a communication network 110. The communication network 110 may provide wired or wireless communications between network nodes such as at least one of: client device 112, a microprocessor 104, a processing device, a processor. Previous example(s) to provide at least one of: deep learning, machine learning of the dental images 108 of at least one of: an e-commerce consumer 133, a person of interest 134 are not provided in a limiting sense. Alternatively, an aggregator 106 may receive the dental images from an e-commerce consumer 133, process the dental images 108, and provide the (annotated) e-commerce consumer dataset and the correlated dental images for e-commerce datasets as at least one of: a desktop application, a workstation application, a cell phone application, a server application, among others. Client application(s) executed by the client device 112 may also include client interface(s) of (or interacting with) an aggregator 106.

The e-commerce provider 132 may also interact with the client application(s) on the client device 112 with a keyboard based input, a mouse based input, a voice based input, a pen based input, and a gesture based input, among others. The gesture based input may include one or more touch based actions such as a touch action, a swipe action, and a combination of each, among others.

While the example system in FIG. 1 has been described with specific components including the microprocessor 104, the aggregator 106, embodiments are not limited to these components or system configurations and can be implemented with other system configuration employing fewer or additional components.

Figure 2:
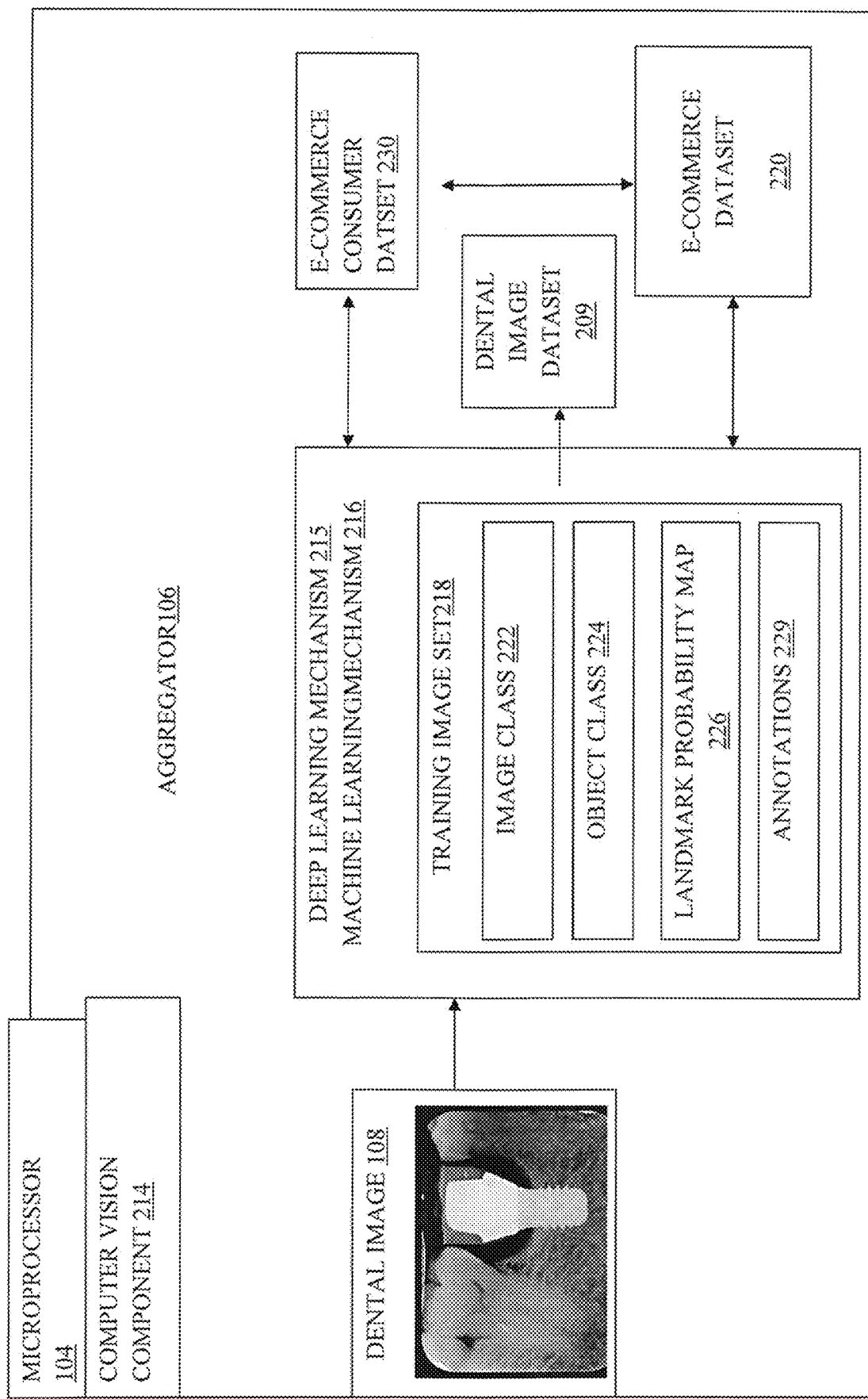
FIG. 2 shows a display diagram illustrating at least one of: a deep learning mechanism, a machine learning mechanism to provide at least one of: a deep learning, a machine learning of dental images for e-commerce, according to an embodiment of the invention.

FIG. 2 shows a display diagram illustrating at least one of: a deep learning mechanism 215, a machine learning mechanism 216 to provide machine learning of dental images for e-commerce. The microprocessor 104 may use a computer vision component 214 to execute an aggregator 106 and process the dental images 108 for e-commerce with a deep learned mechanism 215 and/or a machine learned mechanism 216. The deep learning mechanism 215 and/or the machine learning mechanism 216 may process a dental image 108 with at least one of: an image class 222, object class 224, landmark probability map 226, annotations 229. The deep learning mechanism 215 and/or the machine learning mechanism 216 may compensate for missing information, identify and correct a discrepancy between the dental images 108 with missing information. Further, the deep learning mechanism 215 and/or the machine learning mechanism 216 may process these images with a training image set 218 and compile into an e-commerce consumer dataset 230, a dental image dataset 209 and an e-commerce dataset 220. The machine learning mechanism 216 may identify and correct discrepancies between the correlated e-commerce datasets 220.

In another embodiment at least one of: a microprocessor 104, an aggregator 106, a processor, a processing device is configured to use at least one of: a deep learning mechanism 215, a machine learning mechanism 216 to offer a third party financing company option when at least one of: an e-commerce consumer, a person of interest, a patient has at least one of: a treatment obstacle, a financial obstacle, an insurance obstacle, a payment obstacle. A storage device may be configured for retrieving details of at least one third party financing company and provide it to at least one of: a microprocessor 104, an aggregator 106, a processor, a processing device. Further, at least one of: a microprocessor 104, an aggregator 106, a processor, a processing device may be configured against economic discrimination of at least one of: a treatment obstacle, a financial obstacle, an insurance tier, an insurance payment and offer all option(s) to at least one of: an e-commerce consumer, a person of interest, a patient. Under some circumstances at least one of: a microprocessor 104, an aggregator 106, a processor, a processing device may be configured not to economically discrimination of at least one of: a treatment obstacle, a financial obstacle, an insurance tier, an insurance payment. A circumstance may be unemployment, bankruptcy, divorce, among other. Under common circumstances, offering all option(s) is considered the standard of care by most e-commerce providers.

At least one of: a dental image 108, an e-commerce consumer dataset 220 may be at least one of: correlated, associated to a geographic location with at least one of: a Global Position System (GPS), a Global Navigation System (GLONASS) and provide the geographic location of at least one of: an e-commerce consumer 133, a person of interest 134 over a communication network to at least one of: an insurance company, a business, an e-commerce provider 132, an e-commerce consumer 133, an e-commerce administrator 135, a machine learning entity 170, an e-commerce organization 169, a national security organization, a judiciary agency, a military agency, a government agency, a government, a law enforcement agency, microprocessor, an aggregator, a processor, a processing device.

Further, at least one of: a dental image 108, an e-commerce consumer dataset 220 may be matched to at least one of: a terrorist dataset, a suspected terrorist dataset, a violent criminal dataset, a nonviolent criminal dataset, a cybercrime criminal dataset, a political criminal dataset, a white collar criminal dataset over a communication network to identify the location, with at least one of: a geographic location, a Global Position System (GPS), a Global Navigation System (GLONASS) of at least one of: a dental image 108, an e-commerce consumer dataset 220, an e-commerce consumer 133, a person of interest 134 and provide to at least one of: a national security organization, a judiciary agency, a military agency, a government agency, a government, a law enforcement agency, microprocessor, an aggregator, a processor, a processing device.

Figure 3:
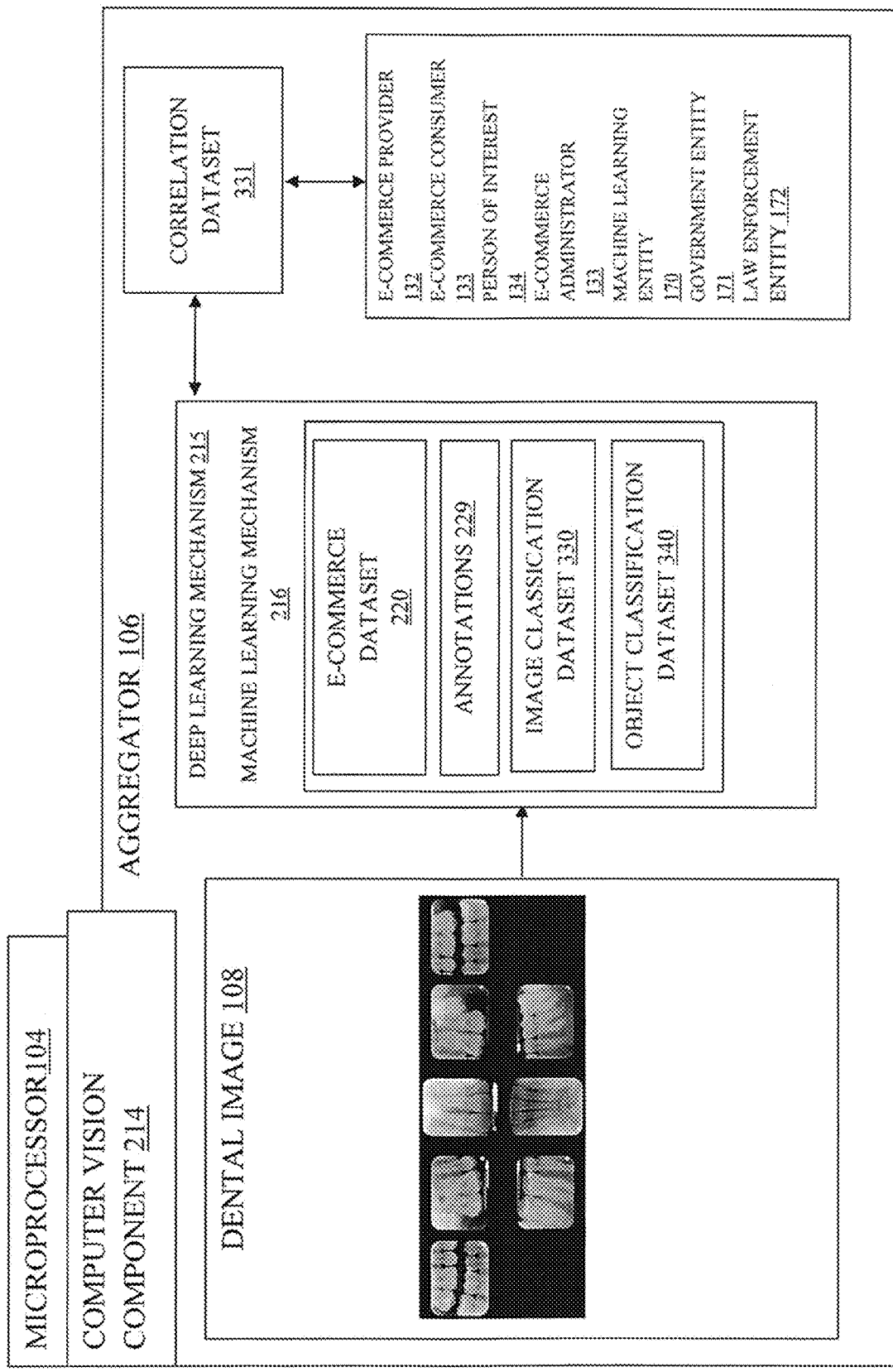
FIG. 3 shows a display diagram illustrating the processing of dental images with e-commerce datasets, annotations, image and object classification datasets to a correlation data set, according to an embodiment of the invention.

FIG. 3 shows a display diagram illustrating at least one of: a deep learning mechanism 215, a machine learning mechanism 216 to provide a correlation dataset 331 from dental images 108 for e-commerce. The microprocessor 104 may process the dental images 108 with the aggregator 106. The aggregator 106 may process the dental images with annotations 229, e-commerce datasets 220, image classifications dataset 330 and object classifications dataset 340 to produce a correlation dataset 331. The correlation dataset 331 may be provided to at least one of: an e-commerce provider 132, an e-commerce consumer 133, an e-commerce administrator 135, machine learning entity 170, an e-commerce organization 169, a government entity 171, a law enforcement entity 172, a person of interest 134.

Figure 4:
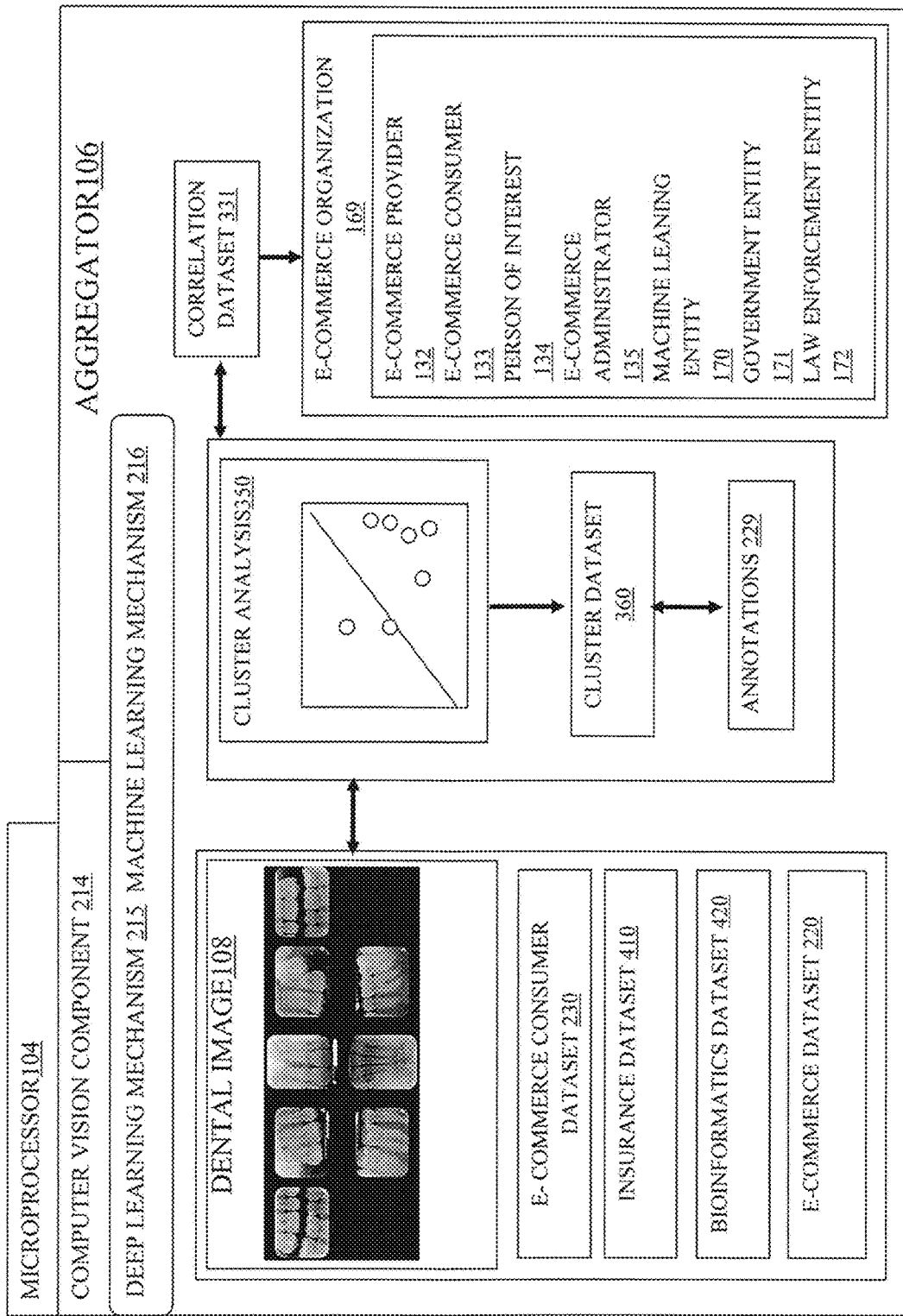
FIG. 4 shows a display diagram illustrating a cluster analysis of dental images and annotations to produce a correlation dataset for an e-commerce provider, an e-commerce consumer, an e-commerce administrator, a machine learning entity, an e-commerce organization, a government entity, a law enforcement entity, a person of interest, according to an embodiment of the invention.

FIG. 4 shows a display diagram of process 400 performing a cluster analysis 350 to produce a correlation dataset 331. The microprocessor may use a computer vision component 214 and at least one of: a deep learning mechanism 215, a machine learning mechanism 216 to process dental image 108. An aggregator 106 (executed by the microprocessor 104) may query and receive at least one of: a dental image 108, an e-commerce consumer dataset 230, an insurance dataset 410, a bioinformatics dataset 420. The e-commerce consumer dataset 230 may include an e-commerce consumer's personal information such as at least one of: an age, a first name, a gender, a middle initial, a last name, a sex, a date of birth, a zip code, an address, a geographic location, a cell phone number, a land line number, a current medication, a previous medication, a social security number, a marital status, an insurance, an insurance identification number, an email address, internet protocol address, a change of insurance, an employer, a change of employment, a change of zip code, a change of the previous medication, a change of a marital status, a change of gender, a location, a Global Position System (GPS) location, a Global Navigation System (GLONASS) location, a chance of location, a passport activity, a visa status, an immigration data, a biometric measurement, an infection status, a disease status, a contact tracing location, a genetic dataset, an internet browsing history, an e-commerce consumer data, a data, among others associated with at least one of: an e-commerce consumer 133, a person of interest 134.

The dental images 108 from an e-commerce consumer 133, a person of interest 134, capture information associated with the dental images 108 for an e-commerce consumer 133 (such as a time, a location, a Global Position System (GPS) location, a Global Navigation System (GLONASS) location, and/or a source, among others), an image class 222 and an object class 224 may be inserted to the e-commerce dataset 220. The aggregator 106 may also identify whether at least one of: an e-commerce consumer 133, a person of interest 134 is informed in regards to a notification obligation such as at least one of: a health insurance portability and accountability act (HIPAA), an end user licensing agreement (EULA), a system and method licensing agreement (SLA), a security token, a swipe authorization, signed consent form by analyzing the e-commerce dataset 220 for attributes associated with the notification obligation.

Furthermore, an aggregator 106 may compare difference(s) between the dental images 108 of at least one of: an e-commerce consumer 133, a person of interest 134 (and associated annotations 229) and the attributes of the e-commerce dataset 220. The dental images 108 may be associated with annotations 229 and processed with a cluster analysis 350. The cluster analysis may be merged into a cluster dataset 360 to be compiled into a correlation dataset 331. The aggregator 106 may recognize, label, and/or classify the correlation dataset 331 of at least one of: an e-commerce consumer 133, a person of interest 134 (and the associated annotations 229) based on the e-commerce dataset 220 (and/or attributes) with a at least one of: a deep learning mechanism 215, a machine learning mechanism 216. The correlation datasets 331 may be provided to at least one of: an e-commerce provider 132, an e-commerce consumer 133, an e-commerce administrator 135, a machine learning entity 170, an e-commerce organization 169, a government entity 171, a law enforcement entity 172, a person of interest 134.

A cluster analysis 350 of the dental images 108 of at least one of: an e-commerce consumer dataset 230, an e-commerce dataset 220 may be performed with a cluster dataset 360 to produce correlated dental images for an e-commerce provider 132, e-commerce consumer 133, e-commerce administrator 135, a machine learning entity 170, an e-commerce organization 169, a government entity, a law enforcement entity, a person of interest 134. The cluster dataset 360 may include annotated information associated with a population and dental classifications associated with the population. The cluster analysis 350 may compare attributes of the e-commerce dataset 220 (such as the capture information, the object class 224, the image class 222, the landmark probability map 226) to elements of the cluster dataset 360. As such, the correlated dental images for an e-commerce provider 132, e-commerce consumer 133, e-commerce administrator 135, a machine learning entity 170, an e-commerce organization 169, a government entity, a law enforcement entity, a person of interest 134 may include attributes of the e-commerce consumer dataset 230.

Furthermore, the cluster analysis 350 may be performed based on at least one of: a spatial detection, a sequential pattern mining, dataset(s) comparison, a data analysis, a statistical data analysis, a Boolean Logic analysis, a fuzzy logic analysis, a machine learned analysis, an anomaly detection analysis mechanism, among others. In addition, the correlated dental images for an e-commerce provider 132 may be merged into the cluster dataset 360 to produce a future cluster analysis with an expanded version of the cluster dataset 360.

In addition, an aggregator 106 may compare difference(s) between the dental images from an e-commerce provider 132 (and associated annotations 229) and the elements of the cluster dataset 360. An aggregator 106 may recognize, label and/or classify the dental images from an e-commerce provider 132 (and the associated annotations 229) based on the element(s) the cluster dataset 360 and/or attributes.

FIG. 4 can be used as an example of a transmission of dental images 108 from at least one of: an e-commerce consumer 133, a person of interest 134 to an e-commerce provider 132 with at least one of: a deep learning service, a machine learning service. Wherein at least one of: an e-commerce provider, a deep learning service, a machine learning service, an e-commerce organization 169 includes at least one of: an insurance service, a dental insurance service. A dental insurance service may include at least one of: an insurance company, an insurance entity, a claims data warehouse. In an example scenario, the machine learning entity 170 may include an insurance machine learning service. A dental insurance service may be an insurance company. At least one of: insurance machine learning service, a dental machine learning service may be provided by at least one of: a dental insurance, a medical insurance organization. An aggregator 106 may correlate a dental image 108 and an e-commerce consumer dataset 230 and analyze with an insurance dataset 410. As such, the correlated dental images of at least one of: an e-commerce consumer 133, a person of interest 134 may include attributes of the e-commerce dataset 220 (such as the dental images 108 for e-commerce and the annotations 229) that are further annotated with elements of the insurance dataset. An aggregator 106 may also format the correlated dental images for an e-commerce provider 132 with an insurance claim. In addition, an aggregator 106 may integrate the correlated dental images of at least one of: an e-commerce consumer 133, a person of interest 134 to a new or an existing insurance claim. The correlation dataset 331 and an e-commerce dataset 220 may also be analyzed and merged (or integrated) into the insurance dataset 410 to expand the insurance dataset 410 for a future analysis.

The microprocessor is further configured to receive a dental image and correlate to at least one of: a tooth number, an American Dental Association (ADA) code, an insurance code, a date, an insurance claim data, a claim identifier, a claim number, a duplicate claim associated with the claim identifier, a provider national identification number, a provider's state license number, a license, a provider identification number to an insurance claim dataset. Further, the microprocessor may at least one of: match and identify an insurance dataset 410 to a dental image, verify tooth numbers and provide to an insurance dataset 410, verify an insurance code and provide to an insurance dataset 410, alert a discrepancies in an insurance dataset and provide an insurance dataset 410 to at least one of: an insurance company, a business, an e-commerce provider, an e-commerce consumer, an e-commerce administrator, a machine learning entity, an e-commerce organization 169, a national security organization, a judiciary agency, a military agency, a government agency, a government, a law enforcement agency, a processing device.

The aggregator 106 may also identify whether the e-commerce consumer and/or the person of interest 134 is informed in regards to a notification obligation such as at least one of: a HIPAA, an EULA, a SLA, a security token, a swipe authorization, signed consent form by analyzing the correlated dental images for e-commerce dataset 220 (annotated with the insurance dataset 410) for attributes associated with the notification obligation. The microprocessor 106 may use quantum encryption of a dental image 108 and an e-commerce dataset 220. The microprocessor 106 may also use quantum encryption of an e-commerce provider's dental image dataset and e-commerce provider's information dataset.

An aggregator 106 may also identify discrepancy(s) between dental insurance claim(s) by analyzing and comparing attributes of the correlated dental images of at least one of: an e-commerce consumer 133, a person of interest 134 and an e-commerce dataset 220 with elements of the insurance dataset 410 including at least one of: American Dental Association (ADA) code(s), an insurance code, a date, an insurance claim data, a claim identifier, a claim number, multiple or duplicate claims (instead of a single claim), a national provider identification number for provider/institution(s), a provider's state license number, a license, among others. Corrective action to merge the discrepancy(s) may be implemented automatically to remove the discrepancy(s) between the correlated dental images for at least one of: an e-commerce consumer 133, a person of interest 134, the e-commerce dataset 220, an insurance claim from the insurance dataset. Alternatively, corrective action may be implemented manually based on at least one of: feedback, input from at least one of: an e-commerce provider 132, an e-commerce consumer 133, an e-commerce administrator 135, a machine learning entity 170, an e-commerce organization 169, a government entity, a law enforcement entity, a person of interest 134 associated with an aggregator 106 regarding the discrepancy(s).

In another example scenario, a machine learning entity 170 may include a bioinformatics machine learning service. A bioinformatics service may be at least one of: a genetic testing service, a genotyping service. The bioinformatics machine learning service may be provided by a bioinformatics organization (such as a personal genomic or research organization). An aggregator 106 may correlate dental image 108, the e-commerce dataset 220 and the correlation dataset 331 (which includes annotations 229) with a bioinformatics dataset 420. As such, the correlated dental images for at least one of: an e-commerce consumer 133, a person of interest 134 may include attributes of an e-commerce dataset 220 (such as the dental images 108 for e-commerce and the annotations 229) that are further annotated with elements of the bioinformatics dataset 420. The correlated dental images for e-commerce dataset 220 may also be merged into the bioinformatics dataset 420 to expand the bioinformatics dataset 420 for a future analysis.

The microprocessor may correlate at least one of: a dental image, a dental image landmark with a genetic dataset to generate a genetic connection. A genetic dataset may include at least one of: a node, genotype, a gene identifier, a gene sequence, a single nucleotide polymorphism, a nucleic acid sequence, a protein sequence, an annotating genome, a shotgun sequence, a periodontal disease, a caries susceptibility, a malocclusion, a pathology, a medical condition. Further, the microprocessor may determining at least one of: a weight associated genetic connection between two directly connected nodes, the shortest genetic connection path, a weight associated with each genetic connection between two directly connected nodes and provide to at least one of: an e-commerce provider, an e-commerce consumer, an e-commerce administrator, a machine learning entity, an e-commerce organization 169, a person of interest 134, a national security organization, a judiciary agency, a military agency, a government agency, a government, a law enforcement agency.

An aggregator 106 may also identify whether at least one of: an e-commerce consumer 133, a person of interest 134 is informed in regards to a notification obligation such as at least one of: a HIPAA, an EULA, a SLA, a security token, a swipe authorization, a signed consent form by analyzing the e-commerce dataset 220 for attributes associated with the notification obligation.

An aggregator 106 may also identify matching elements of the bioinformatics dataset 420 including gene(s) to at least one of: a node, a gene identifier, a gene sequence, single nucleotide polymorphism(s), nucleic acid sequence(s), protein sequence(s) (proteomics), an annotating genome(s), a shotgun sequence, an associated periodontal disease, a caries susceptibility, a malocclusion, a pathology, a medical condition, an impacted tooth, a tooth loss, a missing tooth, congenitally missing tooth, an angle's classification of malocclusion, level(s) of immunoglobulin G (IGG) and immunoglobulin A (IGA), diabetes diagnosis, among others by matching the attributes of the correlated dental images of the e-commerce dataset 220 with elements of the bioinformatics dataset 420. The attributes of the correlated dental images for e-commerce dataset 220 may further be annotated with the elements matched from the bioinformatics dataset 420.

At least one of: a microprocessor, an aggregator, a processor is configured to match and identify the likelihood of a clinical outcome of: at least one of an e-commerce consumer 133, a person of interest 134 with a dental pathology comprising determination of a level of one or more RNA transcripts, or an expression product thereof, in a biological sample obtained from at least one of: an e-commerce consumer 133, a person of interest 134. The method comprises assigning the one or more RNA transcripts, or an expression product thereof, to one or more gene groups selected from a cellular organization gene group, basal epithelia gene group, a stress response gene group, an androgen gene group, a stromal response gene group, and a proliferation gene group. The method further comprises calculating a quantitative score for the patient by weighting the level of the one or more RNA transcripts or an expression product thereof, by their contribution to a clinical outcome and predict the likelihood of a clinical outcome for the patient based on the quantitative score. In an embodiment of the invention, an increase in the quantitative score correlates with an increased likelihood of a negative clinical dental pathology.

The microprocessor 104, which may also be a processor, may be configured to match and identify a dental pathology based on a genetic sample to at least one of: a dental image, an e-commerce dataset 220. Further the microprocessor may match and identify a genetic probability based on at least one of: a dental image 108, an e-commerce dataset 220. The microprocessor may further be configured to match a dental image 108 to a level of RNA transcripts of a gene, that may me quantitatively determined, from at least one of: a tissue, a saliva sample, a sample obtained from at least one of: an e-commerce consumer, a person of interest 134 and at least one of: associate, correlate it to at least one of: a dental image 108, an e-commerce consumer dataset 220. The microprocessor may also compare a normalize level of RNA transcripts of a gene to levels of RNA transcript of at least one reference gene to produce a normalized RNA expression levels and correlate it to at least one of: a dental image 108, an e-commerce consumer dataset 220. The microprocessor may compare a normalized RNA expression level of a gene to a range of normalized RNA expression levels of the same gene obtained from a dental pathology reference set and at least one of: associate, correlate it to at least one of: a dental image 108, an e-commerce dataset 220. Further, the microprocessor may be configured to predict a risk of dental pathology of at least one of: an e-commerce consumer, a person of interest 134 based on the comparison of a normalized RNA expression levels of a gene to a normalized RNA expression levels of a gene and at least one of: associate, correlate it to at least one of: a dental image 108, an e-commerce dataset 220 and provide to at least one of: an e-commerce provider, an e-commerce consumer, an e-commerce administrator, a machine learning entity, an e-commerce organization 169, a person of interest 134, a national security organization, a judiciary agency, a military agency, a government agency, a government, a law enforcement agency, a processor, a processing device.

In another example scenario, an aggregator 106 may verify an authorization by at least one of: an e-commerce consumer 133, a person of interest 134 to allow an analysis of dental images and the e-commerce dataset 220. In response to a determination that at least one of: e-commerce consumer, a person of interest 134 authorized the analysis of the dental images and information dataset for e-commerce, an aggregator 106 may continue with processing the dental images for e-commerce with at least one of: a deep learned image class dataset, a machine learned image class dataset and at least one of: a deep learned object class dataset, a machine learned object class dataset. In response to a failure to verify the authorization by at least one of: e-commerce consumer 133, a person of interest 134 the aggregator 106 may stop operations associated with the dental images for e-commerce.

At least one of: a microprocessor, an aggregator, a processor, a processing device is configured for contact tracing at least one of: an e-commerce consumer 133, a person of interest 134 with an infection status and may be further configured for a contact tracing location. The process may be used for the identification of at least one of: an e-commerce consumer 133, a person of interest 134 who may have come into contact with at least one of: an infected person, a non infected person and subsequent collection of further information about these contacts. By tracing the contacts of at least one of: an e-commerce consumer 133, a person of interest 134 with an infected at least one of: an e-commerce consumer 133, a person of interest 134 and testing them for infection and tracing their global contacts may provide valuable public health safety data. The public health aim may be to reduce infections in the population via this data. Diseases for which contact tracing are commonly performed include tuberculosis, measles, sexually transmitted infections, human immunodeficiency virus (HIV), Herpes simplex virus 1 and 2 (HSV-1 and HSV-2), blood-borne infections, Ebola, bacterial infections, viral infections, parasitic infections, SARS, influenza, Covid-19, among others. The process will at least one of: associate, correlate at least one of: a dental image 108, an e-commerce consumer dataset 220 of at one of: an e-commerce consumer 133, a person of interest 134 with a bioinformatics dataset 420 that may include a disease status and provide over a communication network to at least one of: an insurance company, a business, an e-commerce provider 132, an e-commerce consumer 133, an e-commerce administrator 135, a machine learning entity 170, an e-commerce organization 169, a national security organization, a judiciary agency, a military agency, a government agency, a government, a law enforcement agency, microprocessor, an aggregator, a processor, a processing device. Further at least one of: an association, a correlation of at least one of: a dental image 108, an e-commerce consumer dataset 230 of at least one of: an e-commerce consumer 133, a person of interest 134 with a bioinformatics dataset 420 that may include at least one of: an infection status, a disease status, a contact tracing location and may be correlated to at least one of: a geographic location, a Global Position System (GPS), a Global Navigation System (GLONASS) and may be provide over a communication network to at least one of: an insurance company, a business, an e-commerce provider 132, an e-commerce consumer 133, an e-commerce administrator 135, a machine learning entity 170, an e-commerce organization 169, a national security organization, a judiciary agency, a military agency, a government agency, a government, a law enforcement agency, microprocessor, an aggregator, a processor, a processing device.

Further, biometric sensory measurements of at least one of: a body temperature, a heart rate, a respiration rate, a salivary flow, an eye movement, a voice cadence, a hearing, a sight, a smell, a touch, a taste, a sense, a behavior may be at least one of: correlated, associated with at least one of: a location, a Global Position System (GPS), a Global Navigation System (GLONASS) and provided to the e-commerce dataset 220.

In yet another example scenario, an aggregator 106 may verify compliance of the dental images 108 for e-commerce and/or the correlated e-commerce dataset 220 with a regulatory policy. The aggregate service 106 may also use quantum encryption to verify compliance of the dental images for e-commerce and/or correlate an e-commerce consumer dataset 220. An example of the regulatory policy may include a HIPAA regulation. In response to a determination that the dental images for e-commerce and/or the correlated e-commerce dataset 220 may be compliant with the regulatory policy, an aggregator 106 may provide the correlated dental images of at least one of: an e-commerce consumer 133, a person of interest 134, an e-commerce dataset 220 to the machine learning entity 170 for further processing and to compile a diagnostic probability aid for at least one of: an e-commerce provider 132, e-commerce consumer 133, a person of interest 134, e-commerce administrator 135, a machine learning entity 170, an e-commerce organization 169, a government entity, a law enforcement entity. Alternatively, if the dental images for e-commerce and/or the correlated dental images of the e-commerce dataset 220 may be determined as not in a compliance of the regulatory policy then the dental images for at least one of: an e-commerce consumer 133, an e-commerce dataset 220 may not be provided to at least one of: an e-commerce provider 132, an e-commerce consumer 133, an e-commerce administrator 135, a machine learning entity 170, an e-commerce organization 169, a person of interest 134, a government entity, a law enforcement entity for further processing.

Figure 5:
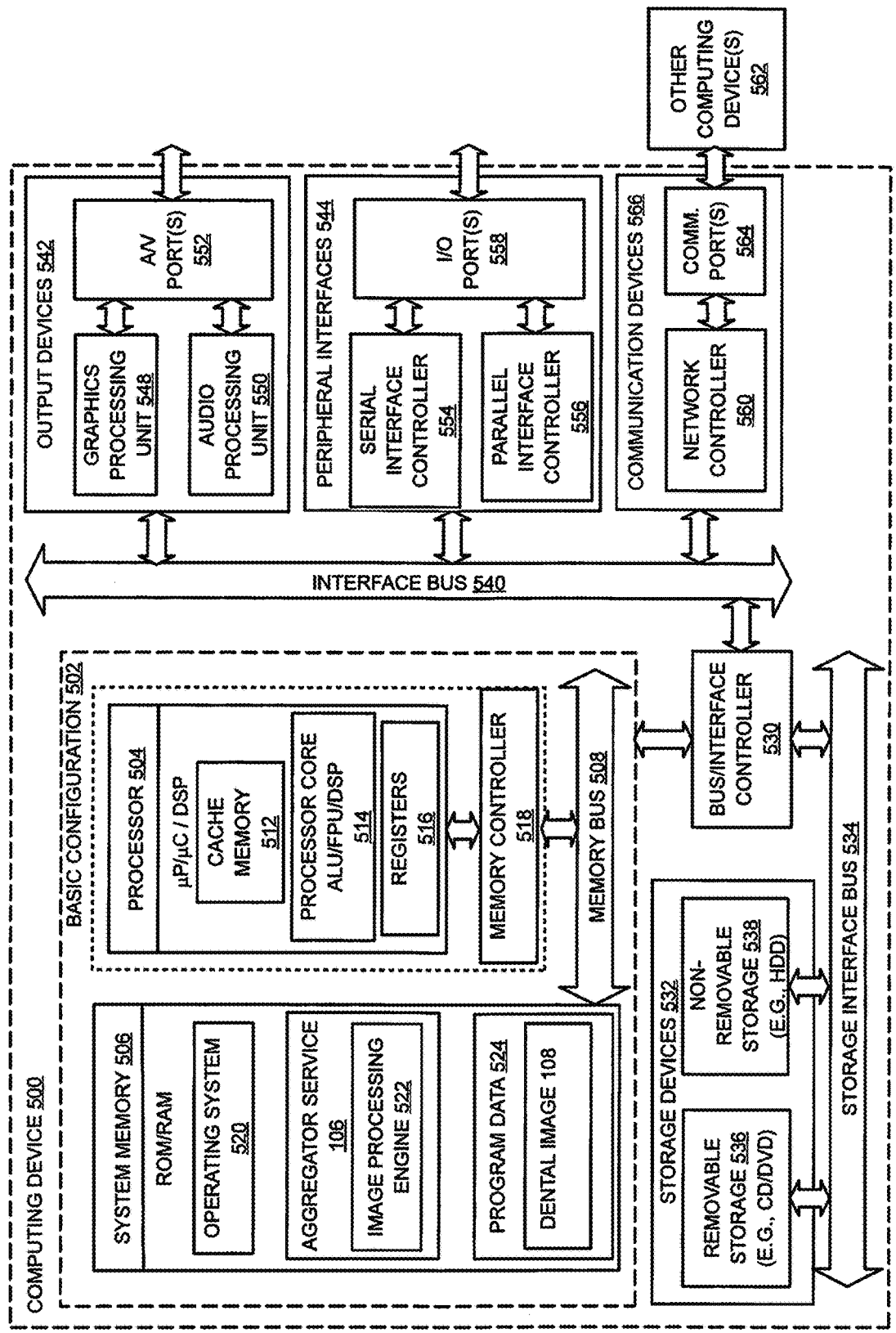
FIG. 5 is a block diagram of an example computing device, which may be used to provide at least one of: a deep learning, a machine learning of dental images for e-commerce, according to an embodiment of the invention.

FIG. 5 is a block diagram of an example computing device, which may be used to provide machine learning of dental images for e-commerce, according to embodiments. For example, computing device 500 may be used as a server, desktop computer, portable computer, smart phone, cell phone, special purpose computer, or similar device. In a basic configuration 502, the computing device 500 may include one or more processors 504 and a system memory 506. A memory bus 508 may be used for communication between the processor 504 and the system memory 506. The basic configuration 502 may be illustrated in FIG. 5 by those components within the inner dashed line.

Depending on the desired configuration, the processor 504 may be of any type, including but not limited to a microprocessor (µP), a microcontroller (µC), a digital signal processor (DSP), or any combination thereof. The processor 504 may include one more levels of caching, such as a level cache memory 512, one or more processor cores 514, and registers 516. The example processor cores 514 may (each) include an arithmetic logic unit (ALU), a floating-point unit (FPU), a digital signal processing core (DSP Core), a graphics processing unit (GPU), or any combination thereof. An example memory controller 518 may also be used with the processor 504, or in some implementations, the memory controller 518 may be an internal part of the processor 504.

Depending on the desired configuration, the system memory 506 may be of any type including but not limited to volatile memory (such as RAM), non-volatile memory (such as ROM, flash memory, etc.), or any combination thereof. The system memory 506 may store and provide an operating system 520, an aggregator 106, and a program data 524. The aggregator 106 may include components such as an image processing engine 522. The image processing engine 522 may execute the instructions and processes associated with the aggregator 106. In an example scenario, the image processing engine 522 may receive a dental image of at least one of: an e-commerce consumer 133, a person of interest 134 from an e-commerce provider 132. Next, the dental images 108 for e-commerce may be processed with at least one of: a deep learning mechanism 215, a machine learning mechanism 216. An image class 222 may be matched to an e-commerce dataset 220 for at least one of: an e-commerce provider 132, an e-commerce consumer 133, a person of interest 134, e-commerce administrator 135, a machine learning entity 170, an e-commerce organization 169, a government entity, a law enforcement entity. The dental images for e-commerce may also be processed with a machine learned object class 224 and landmark probability map 226. An image class 222, an object class 224, a landmark probability map 226 and annotations 229 may be matched to the dental images for at least one of: an e-commerce consumer 133, a person of interest 134. Subsequently, at least one of: the dental images for e-commerce, an image class 222, an object class 224, dental image landmark probability map 226, dental image landmark probabilities, image class landmark probabilities, object class landmark probabilities, spatial landmark probability relationships, object probability landmarks, object probability relationships, landmark probability maps, probability diagnosis, a probability demonstration aid may be inserted to an e-commerce dataset 220 associated with at least one of: e-commerce consumer 133, a person of interest 134. In addition, a cluster analysis 350 of the dental images 108, cluster dataset 360, annotations 229 and the e-commerce dataset 220 may be processed to produce a correlation dataset 331. Furthermore, the correlation dataset 331 may be provided to at least one of: an e-commerce provider 132, an e-commerce consumer 133, an e-commerce administrator 135, a machine learning entity 170, an e-commerce organization 169, a government entity, a law enforcement entity, a person of interest 134 to compile a diagnostic probability aid.

Input to and output out of an aggregator 106 may be transmitted through a communication device 566 that may be communicatively coupled to the computing device 500. The communication device 566 may provide at least one of: wired, wireless communication. The program data 524 may also include, among other data, the dental images for e-commerce 108, or the like, as described herein. The dental images 108 for e-commerce may include at least one of: an x-ray image, a digital image of dental structure(s) of at least one of: an e-commerce consumer 133, a person of interest 134.

The computing device 500 may have additional features or functionality, and additional interfaces to facilitate communications between the basic configuration 502 and any desired devices and interfaces. For example, a bus/interface controller 530 may be used to facilitate communications between the basic configuration 502 and one or more data storage devices 532 via a storage interface bus 534. The data storage devices 532 may be one or more removable storage devices 536, one or more non-removable storage devices 538, or a combination thereof. Examples of the removable storage and the non-removable storage devices may include at least one of: magnetic disk devices, such as flexible disk drives and hard-disk drives (HDDs), optical disk drives such as compact disk (CD) drives or digital versatile disk (DVD) drives, solid state drives (SSDs), tape drives, flash memory, cloud based storage, a cloud computing platform providing a storage service, an open or a closed source platform providing a storage service, a virtual private network (VPN) providing a storage service, an ISO image disk, a cloud based storage service, a redundant array of independent disks (RAID), a USB based disk drive, a USB flash drive, a storage virtualization based storage service, a digital video service, a virtualized server providing a storage service, a super computer providing a storage service, a super computer parallel array providing a storage service, a dental practice management software providing a storage service, a dental digital x-ray software providing a storage service, all future embodiments. Example computer storage media may include volatile and nonvolatile, removable, and non-removable media implemented in any method or technology for storage of information, such as computer-readable instructions, data structures, program modules, all future embodiments, or other data.

The system memory 506, the removable storage devices 536 and the non-removable storage devices 538 are examples of computer storage media. Computer storage media includes, but is not limited to, RAM, ROM, EEPROM, flash memory or other memory technology, CD-ROM, digital versatile disks (DVDs), solid state drives, or other optical storage, quantum memory, magnetic cassettes, magnetic tape, magnetic disk storage or other magnetic storage devices, or any other medium which may be used to store the desired information and which may be accessed by the computing device 500. Any such computer storage media may be part of the computing device 500.

The computing device 500 may also include an interface bus 540 for facilitating communication from various interface devices (for example, one or more output devices 542, one or more peripheral interfaces 544, and one or more communication devices 566) to the basic configuration 502 via the bus/interface controller 530. Some of the example output devices 542 include a graphics processing unit 548 and an audio processing unit 550, which may be configured to communicate to various external devices such as a display or speakers via one or more A/V ports 552. One or more example peripheral interfaces 544 may include a serial interface controller 554 or a parallel interface controller 556, which may be configured to communicate with external devices such as input devices (for example, keyboard, mouse, pen, voice input device, touch input device, etc.) or other peripheral devices (for example, printer, scanner, etc.) via one or more I/O ports 558. An example of the communication device(s) 566 includes a network controller 560, which may be arranged to facilitate communications with one or more other computing devices 562 over a network communication link via one or more communication ports 564. The one or more other computing devices 562 may include servers, computing devices, and comparable devices.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

The computing device 500 may be implemented as a part of a specialized server, mainframe, or similar computer, which includes any of the above functions. The computing device 500 may also be implemented as a personal computer including both laptop computer and non-laptop computer configurations. Additionally, the computing device 500 may include specialized hardware such as an application-specific integrated circuit (ASIC), a field programmable gate array (FPGA), a programmable logic device (PLD), a free form logic on an integrated circuit (IC), among others.

Example embodiments may also include methods to provide at least one of: deep learning, machine learning of dental images for national security utilizing e-commerce. These methods can be implemented in any number of ways, including the structures described herein. One such way may be by machine operations, of devices of the type described in the present disclosure. Another optional way may be for one or more of the individual operations of the methods to be performed in conjunction with one or more human operators performing some of the operations while other operations may be performed by machines. These human operators need not be collocated with each other, but each can be only with a machine that performs a portion of the program. In other embodiments, the human interaction can be automated such as by pre-selected criteria that may be machine automated.

Figure 6:
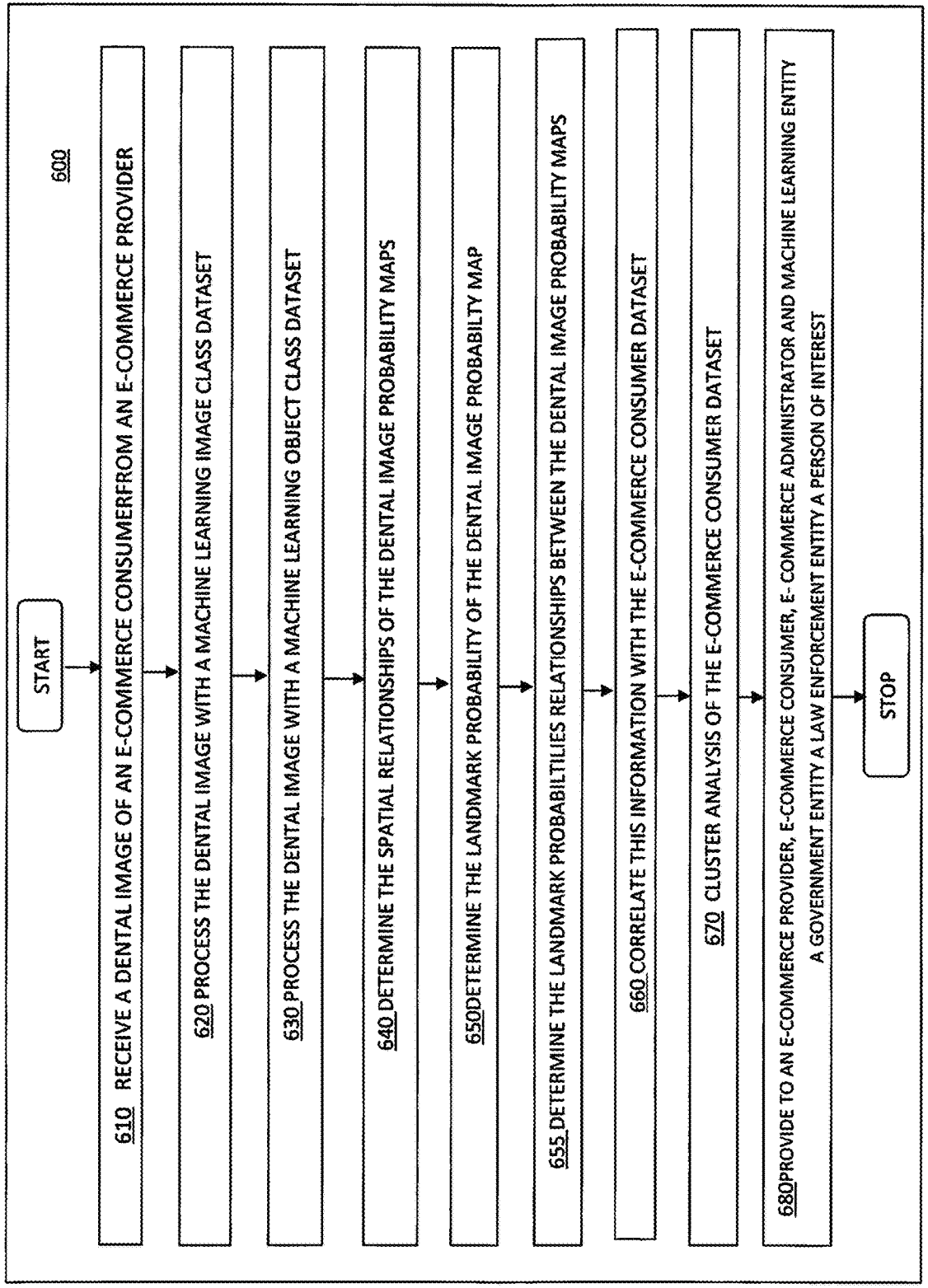
FIG. 6 is a logic flow diagram illustrating a process for providing at least one of: deep learning, machine learning of dental images for national security utilizing e-commerce, according to an embodiment of the invention.

FIG. 6 is a logic flow diagram. Process 600 begins with operation 610, where a aggregator may receive a dental image of at least one of: an e-commerce consumer 133, a person of interest 134 from an e-commerce provider 132. Next, at operation 620, the dental image from an e-commerce provider 132 may processed with at least one of: deep learning, machine learning to match and identify image class landmark probabilities and provide to a dental image dataset. At operation 630, the dental image for e-commerce may be processed to at least one of: deep learn, machine learn to match and identify spatial landmark probability relationships and provide to a dental image dataset. At operation 640, the dental image for e-commerce may also be processed to at least one of: deep learning, machine learning to match and identify object probability landmarks and object probability relationships and provide to a dental image dataset. Operation 650 may use at least one of: deep learning, machine learning to match and identify object probability relationships and provide to a dental image dataset. At operation 655 at least one of: deep learning, machine learning may be used to generate, match and identify dental image landmark probability maps and provide to a dental image dataset. Subsequently, at operation 660, the aggregate server may merge a dental image dataset with an e-commerce consumer dataset to produce an e-commerce dataset 220.

In addition, at operation 670, a cluster analysis of at least one of: an e-commerce dataset, a dental image dataset 209, an e-commerce dataset 220 may be processed with a cluster analysis 350 to produce a correlated large dataset for at least one of: e-commerce providers 132, e commerce consumers 133, e-commerce administrators 135, a machine learning entity 170, an e-commerce organization 169, a government entity, a law enforcement entity, a person of interest 134. At operation 680, the correlated dental images and e-commerce dataset 220 may be provide to an e-commerce dataset to at least one of: an e-commerce provider, an e-commerce consumer, an e-commerce administrator, a machine learning entity, an e-commerce organization 169, a government entity, a law enforcement entity, a person of interest 134. Further, at operation 690, process at least one of: an exchange, a transfer, a buy, a sell of an e-commerce dataset over a communication network.

The operations included in process 600 are for illustration purposes. At least one of: deep learning, machine learning of dental images for national security using e-commerce may be implemented by similar processes with fewer or additional steps, as well as in different order of operations using the principles described herein. The operations described herein may be executed by one or more processors operated on one or more computing devices, one or more processor cores, specialized processing devices, special purpose processors, among other examples.

A method of providing dental images processed with at least one of: deep learning, machine learning for national security using e-commerce is described. The method may include receiving dental images 108 for e-commerce of at least one of: an e-commerce consumer 133, a person of interest 134 from an e-commerce provider 132. The dental images for e-commerce may next be processed with an image class dataset. An image class from at least one of: a deep learned image class dataset, a machine learned image class dataset may be matched to dental images for e-commerce. The dental images for e-commerce may also be processed with at least one of: a deep learning object class, a machine learned object class and provided to an e-commerce dataset 220. An object class and an e-commerce consumer dataset 230 may be matched to the dental images for at least one of: an e-commerce provider 132, e-commerce consumer 133, a person of interest 134, e-commerce administrator 135, a machine learning entity 170, an e-commerce organization 169, a government entity, a law enforcement entity. In addition, an e-commerce consumer dataset 230 of at least one of: an e-commerce consumer 133, a person of interest 134 associated with the dental images 108 for e-commerce may be queried and received from an e-commerce provider 132. Subsequently, the dental images for e-commerce, the image class, the object class, dental image landmark probabilities, image class landmark probabilities, object class landmark probabilities, spatial landmark probability relationships, object probability landmarks, object probability relationships, and dental image landmark probability maps may be correlated with an e-commerce dataset 220. Furthermore, a cluster analysis 350 of the e-commerce dataset 220 may be performed with a cluster dataset 360 to produce a correlated dental images dataset for an e-commerce provider 132. Moreover, the correlated dental images for an e-commerce dataset 220 may be provided to at least one of: e-commerce provider 132, an e-commerce consumer 133, an e-commerce administrator 135, a machine learning entity 170, an e-commerce organization 169, a government entity, a law enforcement entity, a person of interest 134.

Figure 7:
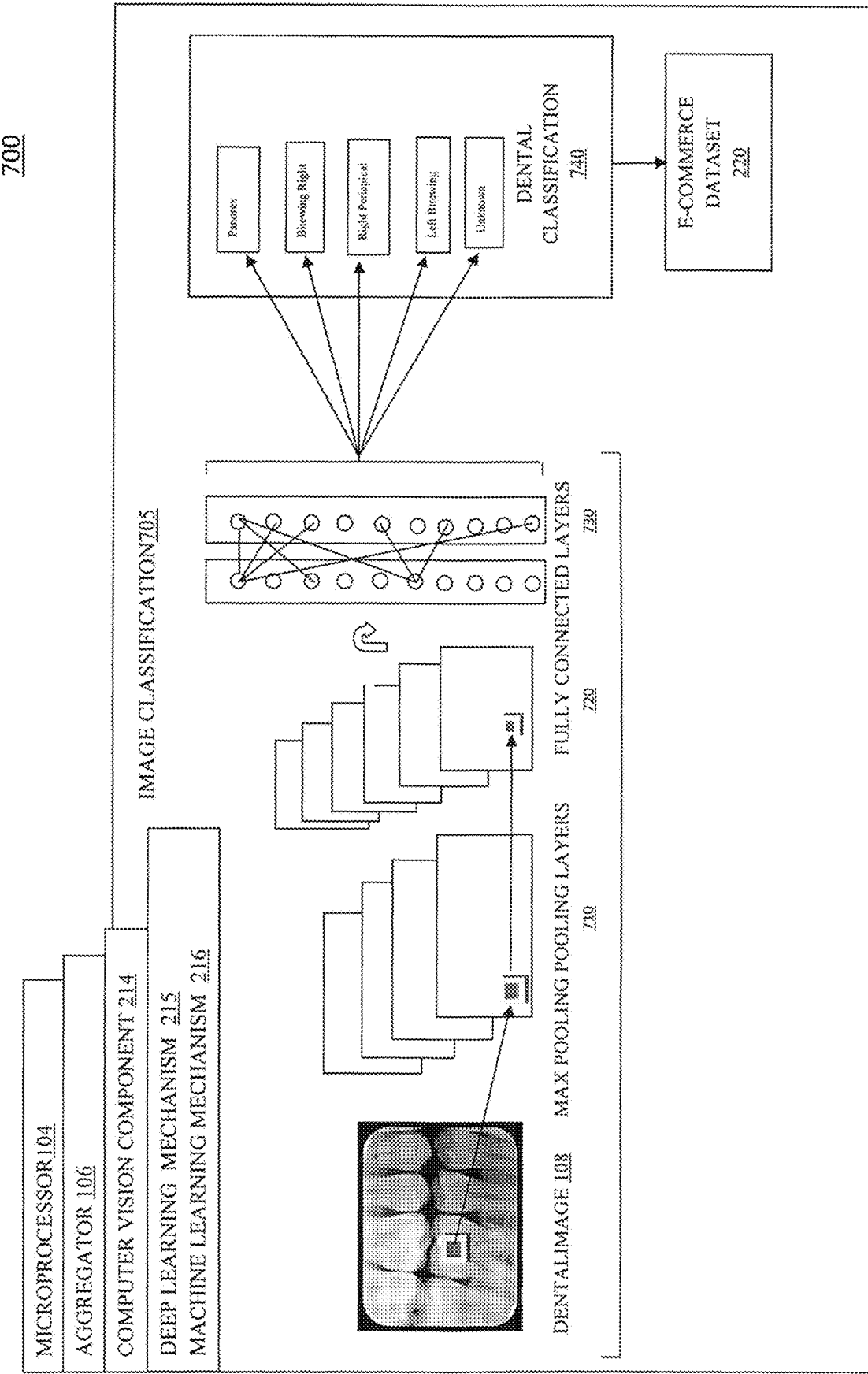
FIG. 7 shows a display diagram of at least one of: a deep learning mechanism, a machine learning mechanism of a dental image being processed with a convolutional neural network to produce a dental classification, according to an embodiment of the invention.

FIG. 7 shows a display diagram illustrating an image classification 705 function to provide at least one of: deep learning, machine learning of dental images for national security utilizing e-commerce is described. The microprocessor 104 may use a computer vision component 214 to execute an aggregator 106 and processes the dental images 108 for e-commerce with an image classification 705 function. Process 700 starts with a first resolution dental image 108 of at least one of: an e-commerce consumer 133, a person of interest 134. At least one of: an e-commerce dental image 108, an e-commerce dataset 220 may be processed with an image classification 705 function to produce a dental classification 740. The image classification 705 may compare attributes of the e-commerce dataset 220 (the capture information, image class 222 and object class 224) to elements of the image classification dataset 330. As such, the correlated dental images for an e-commerce provider 132 may include attributes of the e-commerce dataset 220 (such as the dental images 108 for e-commerce and the annotations 229) that are further annotated with elements of the image classification dataset 330. The process may be repeated and compared to at least one of: a second resolution dental image, a multiple resolution dental images 108.

Furthermore, image classification 705 may be performed based on using a convolutional neural network which may include N images and K classes to produce a training set. A training set classifier may also process dental images of at least one of: an e-commerce consumer 133, a person of interest 134 with a max pooling 710 and pooling layers 720. The dental images of at least one of: an e-commerce consumer 133, a person of interest 134 may then be processed with sliding window components to produce fully connected layers 730 of dental images. The fully connected layers may then be processed into dental classifications 740. Wherein, the dental classifications may include image classes 222 and object classes 224. The dental classifications may be merged with an e-commerce dataset 220. The e-commerce dataset 220 may be provided to at least one of: an e-commerce provider 132, an e-commerce consumer 133, an e-commerce administrator 135, a machine learning entity 170, an e-commerce organization 169, a government entity, a law enforcement entity, a person of interest 134.

Figure 8:
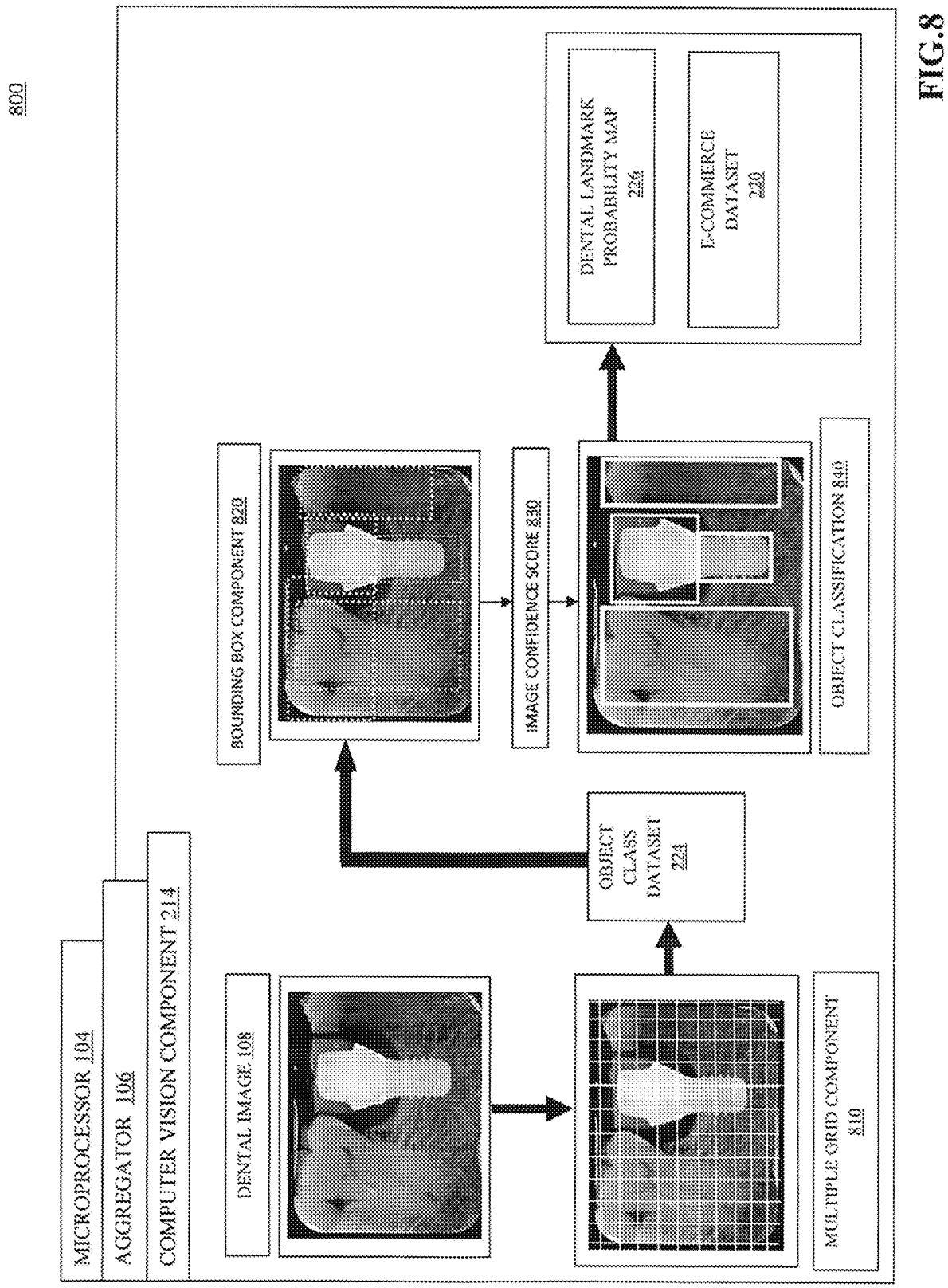
FIG. 8 shows a display diagram of a computer vision component of a dental image being processed with bounding boxes to produce a dental object class, according to an embodiment of the invention.

FIG. 8 shows a display diagram. The microprocessor 104 may use a computer vision component 214 to execute an aggregator 106 and process the dental image 108 with a deep learning mechanism 215 and/or a machine learning mechanism 216. Process 800 begins with a first resolution dental image 108 of at least one of: an e-commerce consumer 133, a person of interest 134 that may be processed with a multiple grid component. The dental image 108 may be further processed by an object class dataset 224. The object class dataset 224 may be processed by a bounding box component 820 to generate bounding boxes around Region of Interest (ROI) of the dental image 108. Individual and/or multiple bounding boxes may be further processed into an object confidence score 830 then processed with an object classification 840. The bounding box component 820 and the object classification 840 may be merged into a dental landmark probability map 226. The process may be repeated and compared to at least one of: a second resolution dental image 108, a multiple resolution dental images 108.

Furthermore, at least one of: a dental image 108, an object class dataset (224), a bounding box component 820, an object confidence score 830, an object classification 840, a dental image probability map 226, an e-commerce dataset 220 may be processed with a convolutional neural network. Examples of a convolutional neural network may include Regional based Convolutional Neural Networks (R-CNN), Fast Regional based Convolutional Neural Networks (Fast R-CNN) and Faster Regional based Convolutional Neural Networks (Faster R-CNN). R-CNN may use object bounding boxes, non object bounding boxes, proposed regions, blobby images regions, a selective search, a support vector machine (SVM), a bounding box component 820, an object confidence score 830, an object classification 840, supervised training and unsupervised training to process dental images. Fast R-CNN may use a ROI pooling, bounding boxes, region proposals, a softmax layer, a bounding box component 820, an object confidence score 830, an object classification 840, supervised training and unsupervised training to process dental images. Faster R-CNN may use region proposal networks (RPN), bounding boxes, a softmax layer, anchors, a ROI pooling, ground truth boxes, a bounding box component 820, an object confidence score 830, an object classification 840, supervised learning and unsupervised learning to process dental images.

At least one of: a deep learning mechanism 215, a machine learning mechanism 216 may at least one of: merge, compare dental images to an object class dataset 224 to generate at least one of: an object confidence score 830, an object classification 840 to produce a dental image probability map 226. At least one of: an object confidence score, an object classification of a dental image processed with CNN may be correlated to a dental landmark probability map 226 and further merged to an e-commerce dataset 220 and provided to at least one of: an e-commerce provider 132, an e-commerce consumer 133, an e-commerce administrator 135 a machine learning entity 170, an e-commerce organization 169, a government entity, a law enforcement entity, a person of interest 134.

Figure 9:
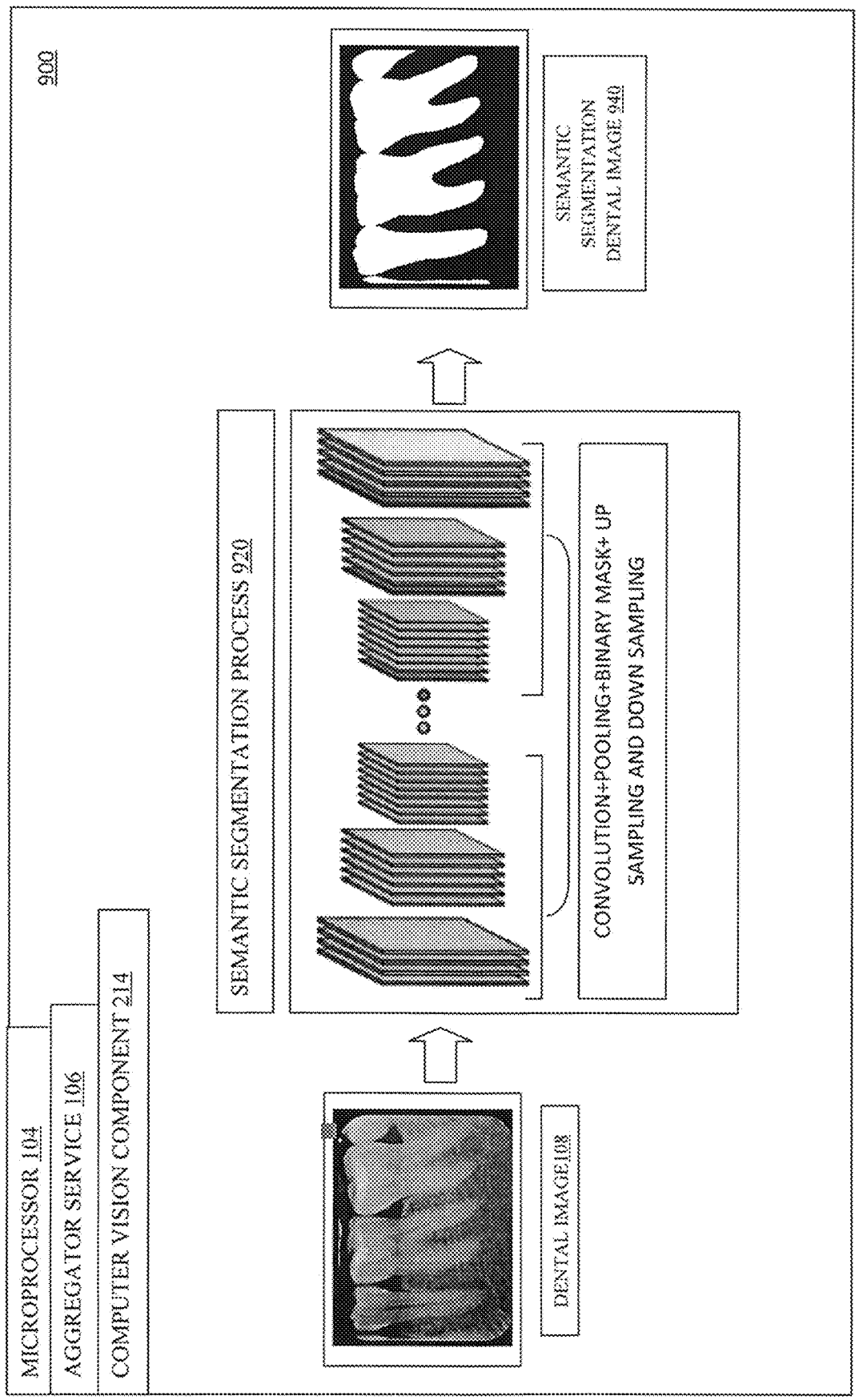
FIG. 9 shows a display diagram of at least one of: a deep learning mechanism, a machine learning mechanism of a dental image being processed with multiple resolutions to produce dental images that show a semantic segmentation process, according to an embodiment of the invention.

FIG. 9 shows a display diagram illustrating semantic segmentation of a dental image 108. The microprocessor 104 may process at least one of: an e-commerce consumer, a person of interest 134's dental image 108 with an aggregator 106, computer vision component 214 and at least one of: a deep learning mechanism 215, a machine learning mechanism 216. Process 900 is an example scenario of a dental image being processed with semantic segmentation. A dental image 108 from at least one of: an e-commerce consumer 133, a person of interest 134 may be processed with a semantic segmentation process 920 to produce a semantic segmentation dental image 940 for an e-commerce provider 132. The semantic segmentation process 900 may correlate attributes of the object class dataset 224, bounding box component 820, image confidence score 830, object classification 840, dental landmark probability map 226, to elements of the semantic segmentation dental image 940. The segmentation dental image 940 may be processed with at least one of: a deep learning mechanism 215, a machine learning mechanism 216. The semantic segmentation dental image 940 may be provided to an e-commerce dataset 220. The dental image 108 of semantic segmentation process 920 may also be processed with transfer learning, stem layers, Atrous spatial pyramid pooling (ASPP) and a Neural Architecture Search (NAS).

Furthermore, semantic segmentation process 920 may be performed based on a using delineation of dental image boundaries, convolution, forward inferences, backward learning, pooling, up sampling and down sampling, class identification (class ID), class identification label (class ID label) and a binary mask. An example of delineated boundaries of a dental image is the black and white junction between the tooth images and a dental image background in semantic segmentation 940. This delineated semantic segmentation example is depicted in black and white. Delineated bounded image may be processed and represented in gray scale or color scale. Delineated bounded image may be colored at the pixel level and an e-commerce consumer's dental image 108 may be processed with an Intersection over Union (IOU) feature. Dental image objects may also be processed with a first resolution, a second resolution and multiple resolutions. The processed semantic segmentation dental images may be correlated to an e-commerce dataset 220 and provided to at least one of: an e-commerce provider 132, an e-commerce consumer 133, an e-commerce administrator 135, a machine learning entity 170, an e-commerce organization 169, a government entity, a law enforcement entity, a person of interest 134. The processed semantic segmentation dental images 940 and the e-commerce dataset 220 may be further processed with an instance segmentation process 1000.

At least one of: a microprocessor, an aggregator, a processing device, a processor may be configured to process with at least one of: an image pyramid, pyramid representation, a Gaussian pyramid, a Laplacian pyramid, Steerable pyramid, Pyramid generation may use at least one of: smoothing kernels, binomial kernels, Gaussian blur, textured synthesis, image compression, object recognition, Gaussian filter, steerable filters, scale-space representations, bilateral filter.

At least one of: a microprocessor, an aggregator, a processing device, a processor may receive a dental image 108 and match and identify a first dental image at a first resolution with at least one of: an image, a class, a landmark, a spatial relationship, an object, an object probability, a map and provide to a dental image dataset 209. At least one of: a microprocessor, an aggregator, a processing device, a processor may match and identify a second dental image at a second resolution with at least one of: an image, a class, a landmark, a spatial relationship, an object, an object probability, a map and provide to a dental image dataset. At least one of: a microprocessor, an aggregator, a processing device, a processor may merge a first dental image and a second dental image into a multiple dental image dataset 209. At least one of: a microprocessor, an aggregator, a processing device, a processor may match and identify a multiple dental image dataset at a multiple resolution with at least one of: an image, a class, a landmark, a spatial relationship, an object, an object probability, a map and provide to a dental image dataset 209. At least one of: a microprocessor, an aggregator, a processing device, a processor may correlate a dental image dataset 209 with an e-commerce consumer dataset 230 to provide to an e-commerce dataset 220. Wherein, an e-commerce consumer dataset 230 includes at least one e-commerce consumer data. Further, the processor may correlate an e-commerce dataset 220 with at least one of: a terrorist dataset, a suspected terrorist dataset, a violent criminal dataset, a nonviolent criminal dataset, a cybercrime criminal dataset, a political criminal dataset, a white collar criminal dataset to produce a person of interest 134 dataset.

Figure 10:
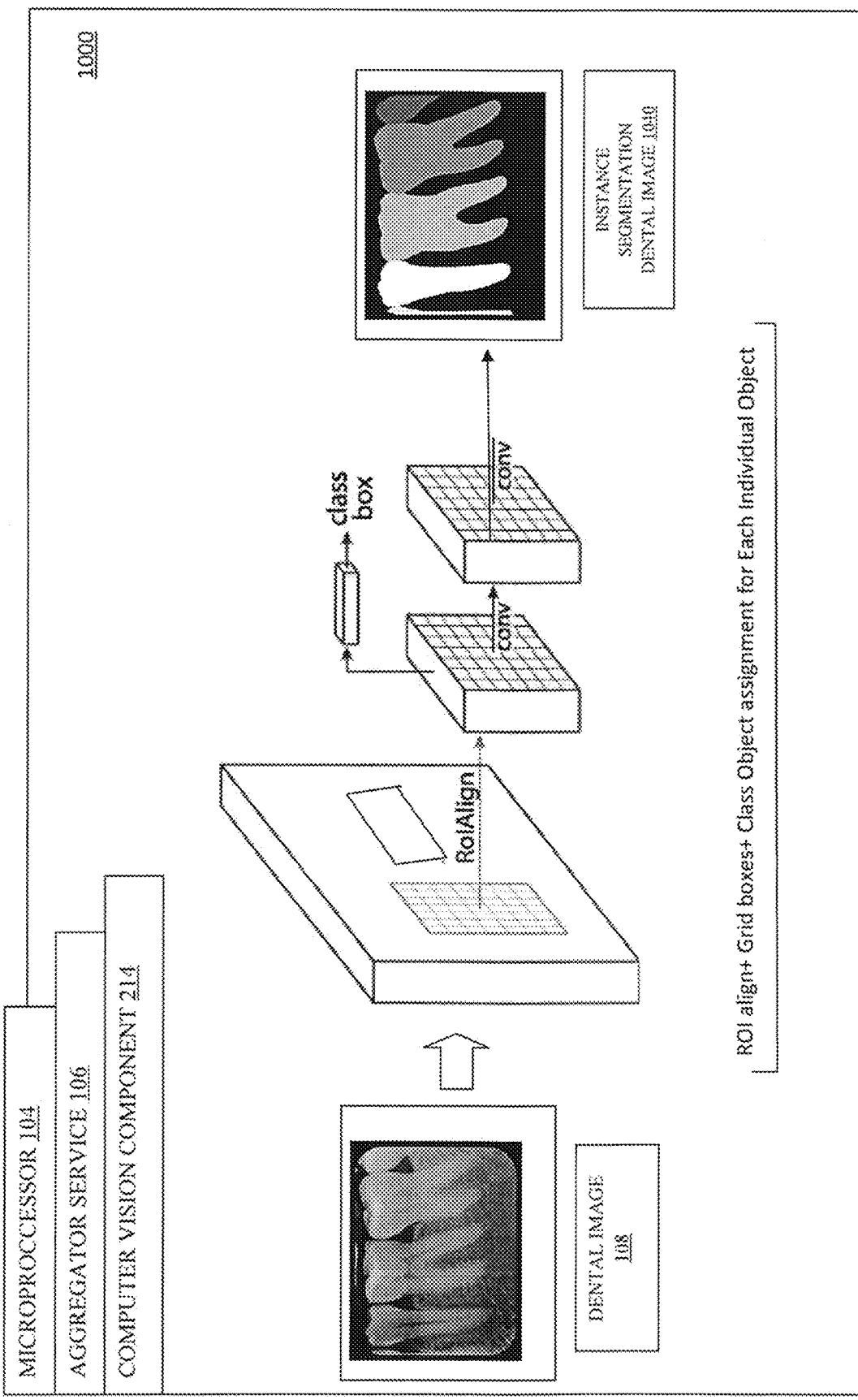
FIG. 10 shows a display diagram of at least one of: a deep learning mechanism, a machine learning mechanism of a dental image being processed with multiple resolutions to produce dental images that show an instance segmentation process, according to an embodiment of the invention.

FIG. 10 shows a display diagram illustrating an instance segmentation process 1000 of a dental image 108 for e-commerce. The microprocessor 104 may process e-commerce dental images 108 with an aggregator 106, computer vision component 214, a deep learning mechanism 215 and a machine learning mechanism 216. A dental image 108 may be processed with an instance segmentation function to produce an instance segmentation dental image 1040 for an e-commerce provider 132, e-commerce consumer 133, a person of interest 134, e-commerce administrator 135, a machine learning entity 170, an e-commerce organization 169, a government entity, a law enforcement entity. The instance segmentation process 1000 may correlate attributes of the e-commerce dataset 220.

Furthermore, instance segmentation process 1000 may be performed with overlapping objects, multiple overlapping objects, different backgrounds, a Region of Interest Align (ROI Align), a class awareness, an instance awareness, anchor boxes, ground truth boxes, object confidence scores and binary masks generated for individual and/or multiple objects. Instance segmentation may be processed by Region proposed networks (RPN), Featured Pyramid Networks (FPN) and Fully Convolutional Networks (FCN). Delineated dental image objects may also be processed in color, gray scale and black and white resolutions.

An example of delineated boundaries of a dental image is shown at the junction between the black background and each gray scale tooth image in instance segmentation dental image 1040. This delineated instance segmentation example depicts five teeth each in a different gray scale. Each delineated bounded image may also be processed and represented in gray scale or color scale. Further, this example may be processed into bounding boxes in different colors. The processed instance segmentation dental images 1040 may be correlated to an e-commerce dataset 220 and provided to at least one of: an e-commerce provider 132, an e-commerce consumer 133, an e-commerce administrator 135, a machine learning entity 170, an e-commerce organization 169, a person of interest 134, a government entity, a law enforcement entity.

The microprocessor is configured to at least one of: deep learning, machine learning of a dental image for e-commerce includes processing the dental image with at least one of: a machine learning process, a deep learning process, a computer vision process, a sliding window component, a multiple grid component, a bounding box component, an image classification component configured to generate a dental image confidence score, an object classification component configured to generate a dental object confidence score, a value mechanism component configured to generate a treatment confidence score, a value mechanism component configured to generate a dental product confidence score, a value mechanism component configured to generate a real time dental treatment recommendation, a value mechanism component configured to generate a real time dental product recommendation, a semantic segmentation component configured to generate a semantic segmentation, an instance segmentation component configured to generate an instance segmentation, a supervised learning component configured to annotate, an unsupervised learning component configured to annotate, a recurrent neural network component (RNN) configured to analyze a dataset, an independent neural network component (INDRNN) configured to analyze a dataset, a deep forest decision tree configured to analyze a dataset, a processor configured for a system of memory of dataset, a processor configured for an artificial intelligence system with memory, a processor configured for a system of reactive memory, a processor configured for a system of non reactive memory, a processor configured for a system of rewards training, a processor configured for a system of transfer learning, a processor configured with an object tracking mechanism configured to track object, a processor configured for natural language processing (NLP), a processor configured to use non-linear regression, an image pyramid, a processor configured to use exponential powers laws, a processor configured to use a geometric series, a processor configured to use a binomial distribution. Further, a microprocessor may be configured after processing the above mentioned the dental mages to exchange at least one of: a dental image, an e-commerce consumer dental image, a dental image dataset, an e-commerce consumer dataset, an e-commerce dataset, a person of interest dataset 1050 with a mobile device.

At least one of: a microprocessor, an aggregator, a processing device, a processor may be configured to processing with at least one of: an image pyramid, pyramid representation, scale space representation, multi-resolution analysis, pyramid generation, pyramid kernels, application pyramids. Pyramid generation may use a lowpass pyramid or a bandpass pyramid or both.

At least one of: a microprocessor, an aggregator, a processing device, a processor may match and identify a first dental image at a first resolution to at least one of: a dental image landmark probabilities dataset, an image class landmark probabilities dataset, an object class landmark probabilities dataset, a spatial landmark probability relationships dataset, an object probability landmarks dataset, an object probability relationships dataset, a dental image landmark probability map, a dental image landmark probability map dataset and provide to a dental image dataset 209. The microprocessor may continue to match and identify a second dental image at a second resolution to at least one of: a dental image landmark probabilities dataset, an image class landmark probabilities dataset, an object class landmark probabilities dataset, a spatial landmark probability relationships dataset, an object probability landmarks dataset, an object probability relationships dataset, a dental image landmark probability map, a dental image landmark probability map dataset and provide to a dental image dataset 209. The first dental image and second dental image may be provided to a multiple dental image dataset. The microprocessor may match and identify a multiple dental image dataset at a multiple resolution to at least one of: a dental image landmark probabilities dataset, an image class landmark probabilities dataset, an object class landmark probabilities dataset, a spatial landmark probability relationships dataset, an object probability landmarks dataset, an object probability relationships dataset, a dental image landmark probability map, a dental image landmark probability map dataset and provide to a dental image dataset 209. Further, the microprocessor may correlate a dental image dataset 209 with an e-commerce consumer dataset 230 to produce an e-commerce dataset 220.

Figure 11:
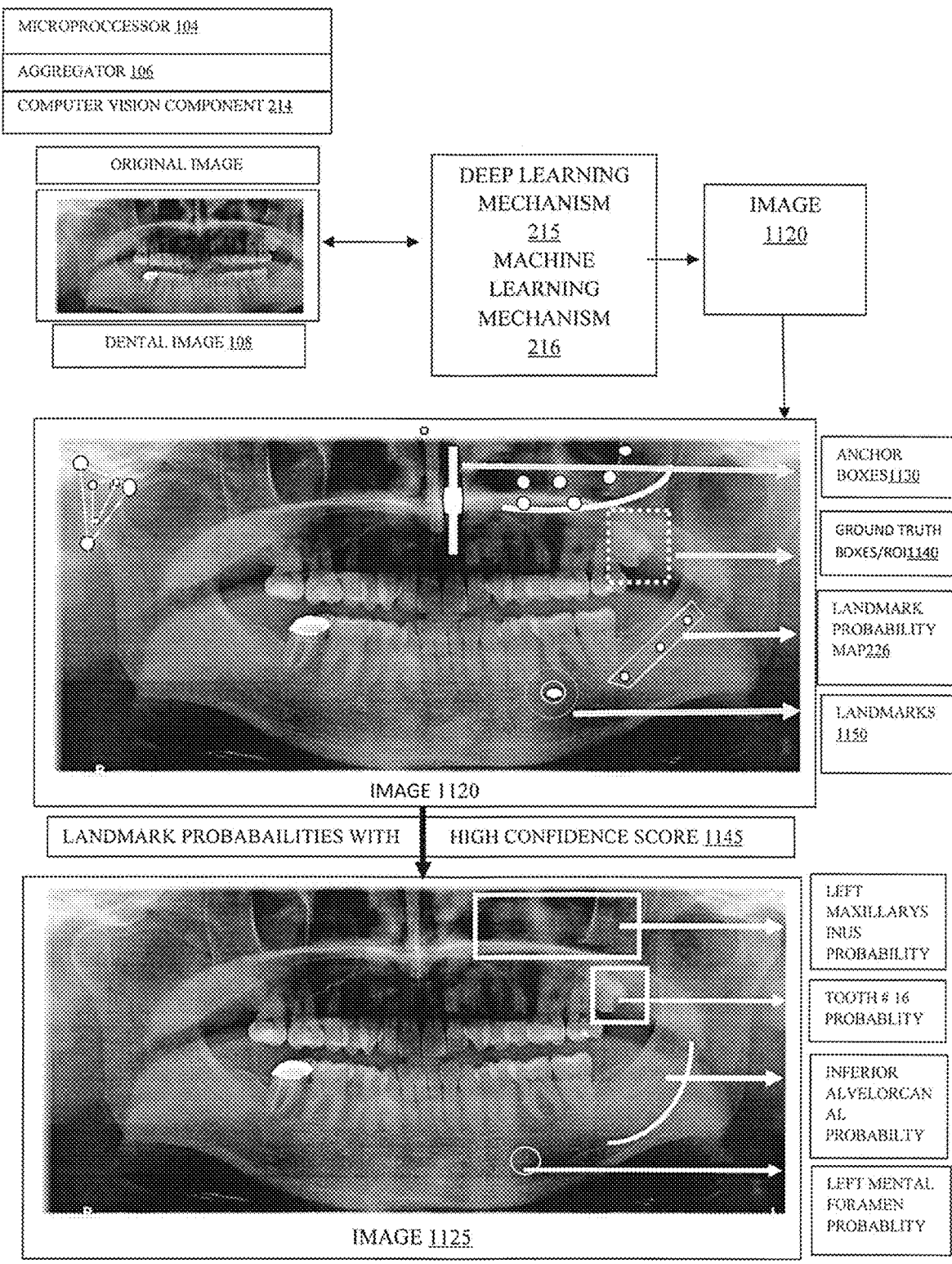
FIG. 11 shows a display diagram of at least one of: a deep learning mechanism, a machine learning mechanism of a dental image being processed with anchor boxes, ground truth boxes, landmarks and landmark probability maps to produce landmark probabilities with high confidence scores, according to an embodiment of the invention.

FIG. 11 shows a display diagram of at least one of: a deep learning mechanism 215, a machine learning mechanism 216 to produce high confidence landmark probability score 1145 for e-commerce. An aggregator 106 (executed by the microprocessor 104) may use computer vision component 214 to analyze the dental image 108. In this example at least one of: a deep learning, a machine learning of dental images may be processed with a function to produce landmark probability maps 226. Wherein, a landmark 1150 may be at least one of: a pixel, a voxel, a loci, a class, an image class, an object class, an object. A dental image landmark may be outlined with pixel delineation, a straight line, a curved line, a circle, a square, a rectangle, a triangle a polygon. The dental image 108 may be processed with anchor boxes 1130, ground truth boxes 1140, landmarks 1150, predictive landmarks and landmark probability map 226. Image 1120 shows ground truth boxes 1140, anchor boxes 1130, landmarks 1150 and a landmark probability map 226 placed around high probability anatomical structures. One or more convolutional layers may be configured to extract predictive landmarks from the training of dental images. A convolutional neural network may learn dental image class probabilities maps and dental object class probability maps of the dental image 108. The convolutional neural network may process the dental image 108 with at least one of: Euclidean geometry, extremely randomized forest functions to produce a dental image landmark probability map and spatial relationships of the dental image landmark probability maps. A different dental image landmark probability map is learned for each dental image landmark and the aggregate server may compensate for at least one of: distorted information, missing information. The convolutional neural network may then process the dental image class 222 and object class 224 with a machine learning spatial relationship function to determine the spatial relationships between the locations of the dental landmarks and produce a plurality of dental image landmark probability maps. Further the convolutional neural network may at least one of: deep learn, machine learn object probability relationships between the locations of the dental images probability maps and at least one of: deep learn, machine learn object probability relationships between the locations of the dental image probability maps. An example of a high confidence value for a dental object is shown in image 1125 of a left maxillary sinus. Other examples in dental image 1125 with high confidence scores may include a left inferior alveolar nerve canal, $3^{rd}$ molar #16 and the left mental foremen. The aggregate server may provide at least one of: a probability diagnosis, a probability demonstration aid from the plurality of dental image landmark probability maps to at least one of: an e-commerce provider 132, e-commerce consumer 133, a person of interest 134, an e-commerce administrator 135, a machine learning entity 170, an e-commerce organization 169, a government entity, a law enforcement entity. The processed landmark probability maps may be correlated to an e-commerce dataset 220 and provided to at least one of: an e-commerce provider 132, an e-commerce consumer 133, an e-commerce administrator 135, a machine learning entity 170, an e-commerce organization 169, a government entity, a law enforcement entity, a person of interest 134.

Figure 12:
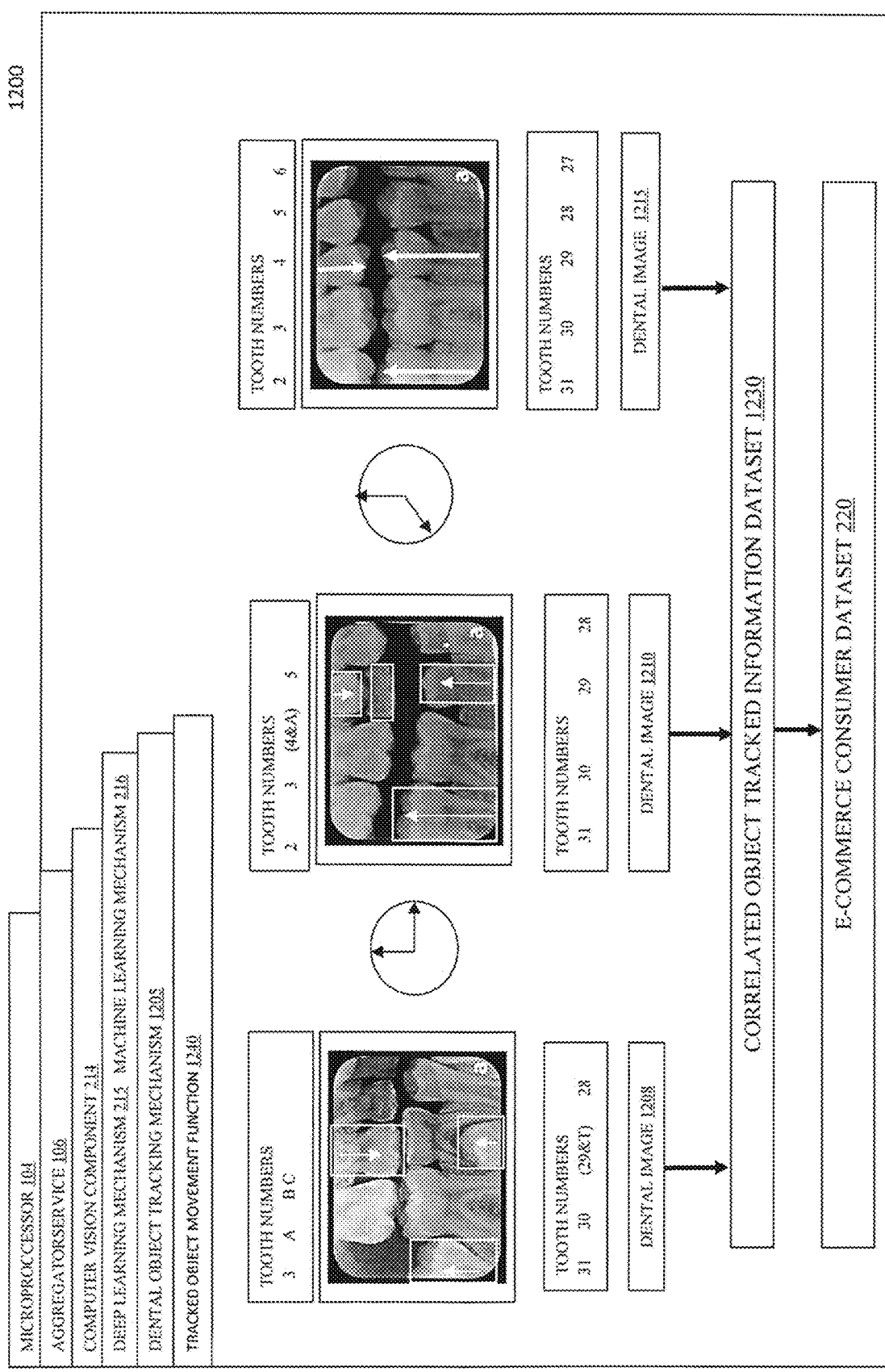
FIG. 12 shows a display diagram of at least one of: a deep learning mechanism, a machine learning mechanism that is object tracking a first dental image then object tracking a second dental image according to the embodiment of the invention.

FIG. 12 shows a display diagram (process 1200) illustrating a dental object tracking mechanism 1205. The microprocessor 104 may use a computer vision component 214 and at least one of: a deep learning mechanism 215, a machine learning mechanism 216 to execute an aggregator 106 and process the dental image 1208 for at least one of: an e-commerce, a person of interest 134 with a dental object tracking mechanism 1205. Dental image 1208 of at least one of: an e-commerce consumer 133, a person of interest 134 may be processed with a dental object tracking mechanism 1205. Object tracking may use pooling layers, fully connected layers, multiple resolutions, multiple grid components, bounding boxes, a classified image score, an object classification, a semantic segmentation, a instance segmentation, anchor boxes, ground truth boxes, dental image landmark probabilities, image class landmark probabilities, object class landmark probabilities, spatial landmark probability relationships, object probability landmarks, object probability relationships, and dental image landmark probability maps. Further, an object tracked image may be at least one of: a frame, an image, a layer, a slice, a section. A first time interval, dental image 1208 of an e-commerce consumer may be processed and compared with a second time interval dental image 1210 of at least one of: an e-commerce consumer 133, a person of interest 134. The second dental image 1210 of at least one of: an e-commerce consumer 133, a person of interest 134 may be compared with a third time interval dental image 1215 of an e-commerce consumer. Dental images 1208, 1210 and 1215 may be processed and compared with a tracked object movement function 1240. The tracked object movement function 1240 may further track multiple dental images of at least one of: an e-commerce consumer 133, a person of interest 134 over time. The tracked object movement function 1240 may provide the tracked dental image object movements to a correlated object tracked information dataset 1230. Correlated object tracked information dataset 1230 may be provided to an e-commerce dataset 220.

In an example scenario dental image 1208, 1210 and 1215 are dental images of the same e-commerce consumer taken at different time intervals in the same anatomical location. Dental image 1208, 1210 and 1215 may be processed with object classification 840, ROI and ground truth boxes. Dental image 1208 shows a mixed dentition of primary teeth A, B, C and T and adult teeth 3, 28, 29, 30 and 31. Dental image 1210 was taken at a later period in time. Dental image 1210 shows that the primary teeth B and T were exfoliated and primary tooth A is in the process of erupting from the upward eruption force of adult tooth 4. In addition tooth number 2 is not present in dental image 1208 and has erupted into position in dental image 1210. Further, adult tooth number 31 is only partially erupted in dental image 1208. In dental image 1210 number 31 has fully erupted into an adult occlusion. Dental image 1215 was taken in a later period of time after dental image 1210. Dental image 1215 shows no primary teeth and only adult teeth 2,3,4,5,6,27, 28,29,30 and 31. The tracked object movement function 1240 may track, measure and compare the primary and adult teeth movements and provide these object tracking movements to the correlation object tracked information dataset 1230. The correlation object tracked information dataset 1230 may compare the e-commerce consumer object tracked image to a large dataset of dental object tracked movements. The correlation object tracked information dataset 1230 may provide the datasets to an e-commerce dataset 220.

In another example, dental object tracking process 1205 may be performed based on using convolutional neural networks and at least one of: a deep learning mechanism 215, a machine learning mechanism 216. The dental object tracking process 1205 may be further processed with bounding boxes, an image resizing, multiple resolutions, a ROI, a ROI Align, anchor boxes, Stacked Auto Encoders (SAE), a speech recognition and language processing. Dental image 1208 may be processed with corners, an edge mapping, a roundness, a smoothness, a sharpness and a blurriness and merged into an e-commerce dataset 220.

Dental image objects may be processed at a first resolution and object tracked. The same dental image object may be processed at a second resolution and object tracked. Multiple dental image objects may be processed with multiple resolutions and object tracked. This process may continue and an object tracking dataset may be provided to at least one of: an e-commerce provider 132, an e-commerce consumer 133, an e-commerce administrator 135, a machine learning entity 170, an e-commerce organization 169, a government entity, a law enforcement entity, a person of interest 134.

In addition, at least one of: a microprocessor, an aggregator, a processing device, a processor may use the tracked object movement function 1240 of a dental image 108(s) obtained at different geographic locations of at least one of: an e-commerce consumer 133, a person of interest 134 based on a geographic location technologies such as at least one of: a Global Position System (GPS), Global Navigation System (GLONASS), among others may be provided over a communication network to at least one of: an insurance company, a business, an e-commerce provider 132, an e-commerce consumer 133, an e-commerce administrator 135, a machine learning entity 170, an e-commerce organization 169, a national security organization, a judiciary agency, a military agency, a government agency, a government, a law enforcement agency, microprocessor, an aggregator, a processor, a processing device. Further, at least one of: an insurance company, a business, an e-commerce provider 132, an e-commerce consumer 133, an e-commerce administrator 135, a machine learning entity 170, an e-commerce organization 169, a national security organization, a judiciary agency, a military agency, a government agency, a government, a law enforcement agency may track at least of: a e-commerce consumer 133, a person of interest 134 based on at least one of: a geographic location, a Global Position System (GPS), Global Navigation System (GLONASS) and at least one of: a dental image 108, an e-commerce dataset 220. In addition at least one of: a microprocessor, an aggregator, a processing device, a processor is configured to notify at least one of: an insurance company, a business, an e-commerce provider 132, an e-commerce consumer 133, an e-commerce administrator 135, a machine learning entity 170, an e-commerce organization 169, a national security organization, a judiciary agency, a military agency, a government agency, a government, a law enforcement agency, may recognize when at least one of: an e-commerce consumer 132, a person of interest 134 has moved or changed address based on at least one of: a geographic location, a Global Position System (GPS), a Global Navigation System (GLONASS) that is associated to at least one of: a dental image 108, an e-commerce dataset 220.

Figure 13:
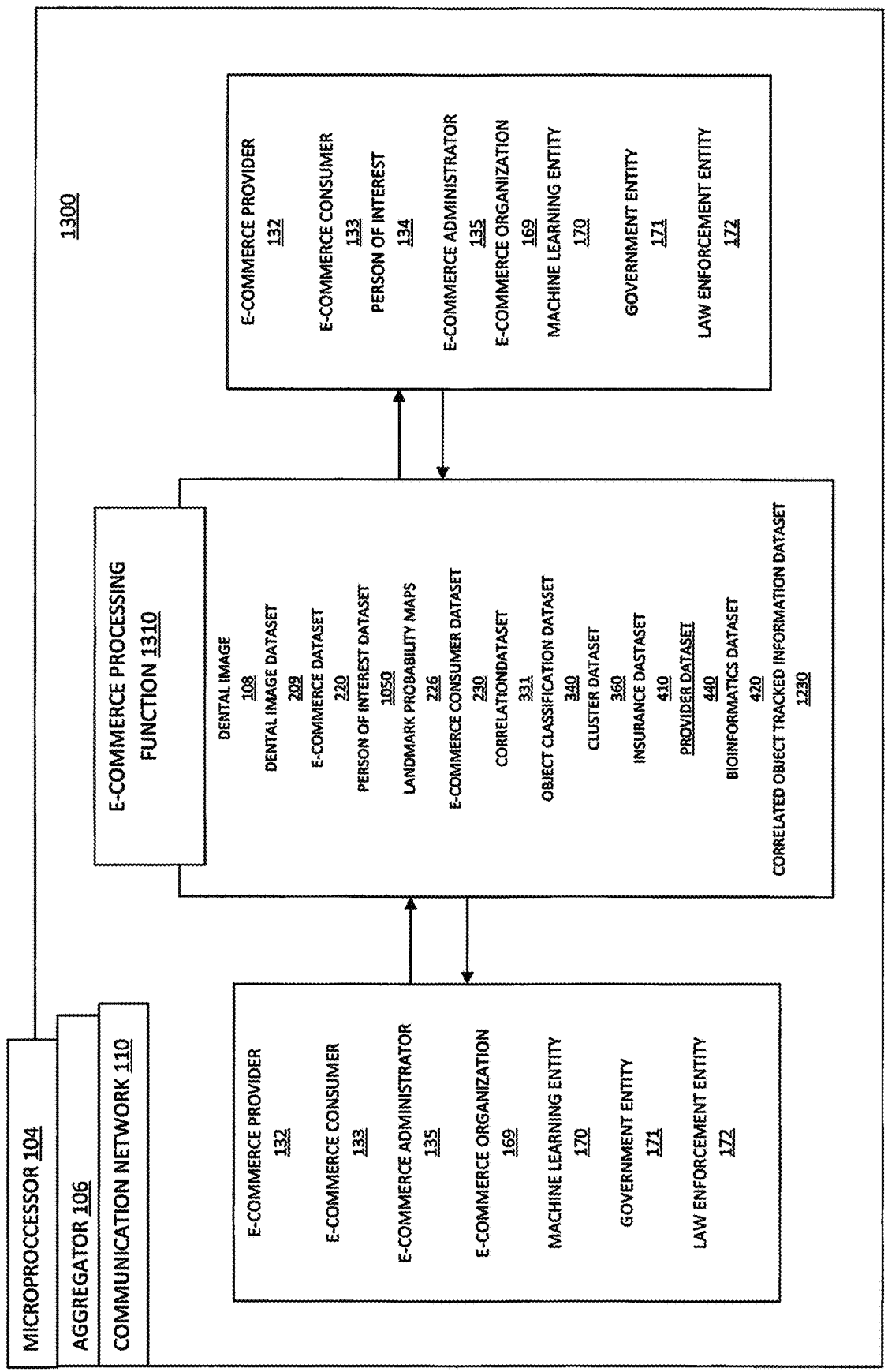
FIG. 13 shows a display diagram of an e-commerce processing function transferring datasets between e-commerce providers, e-commerce consumers, e-commerce administrators, a machine learning entity, an e-commerce organization, a government entity, a law enforcement entity, a person of interest according to an embodiment of the invention.

FIG. 13 shows a display diagram. The microprocessor 104 may use a communication network 110 to execute an aggregator 106 and process a transaction of at least one of: an exchange, a transfer, a buy, a sell with at least one of: a dental image 108, dental image dataset 209, an e-commerce dataset 220, a person of interest dataset 1050, a landmark probability map 226, an e-commerce consumer dataset 230, a correlation dataset 331, an object classification dataset 340, a cluster dataset 360, an insurance dataset 410, a provider dataset 440, a bioinformatics dataset 420, a correlated object tracked information dataset 1230, of at least one of: an e-commerce consumer 133, a person of interest 134 over a communication network 110, wherein a communication network includes at least one of: a secure communication network, an encrypted communication network, the internet, an intranet, an extranet, an internet, an internet transaction service, an online transaction service, a mobile network, a wireless network, an online transaction processing (OLTP) service, an online analytical processing (OLAP) service, a transaction platform, an internet transaction platform. Further, the communication network 110 may at least one of: an exchange, a transfer, a buy, a sell at least one of: a dental image 108, an e-commerce consumer dental image, a dental image dataset 209, an e-commerce dataset 220, a person of interest 134 dataset, a landmark probability map 226, an e-commerce consumer dataset 230, a correlation dataset 331, an object classification dataset 340, a cluster dataset 360, an insurance dataset 410, a provider dataset 440, a bioinformatics dataset 420, a correlated object tracked information dataset 1230 over at least one of: a secure communication network, an encrypted communication network, the internet, an intranet, an extranet, an internet, an internet transaction service, an online transaction service, a mobile network, a wireless network, an online transaction processing (OLTP) service, an online analytical processing (OLAP), a transaction platform. Process 1300 may begin with at least one of: an e-commerce provider 132, an e-commerce consumer 133, an e-commerce administrator 135, a machine learning entity 170, an e-commerce organization 169, a government entity 171, a law enforcement entity 172, a person of interest 134 uploading and/or down loading at least one of: a dental image 108, an e-commerce dataset 220 with an e-commerce processing function 1310. The e-commerce processing function 1310 may upload and/or down load dental images 108 and e-commerce datasets 220 to at least one of: an e-commerce provider 132, an e-commerce consumer 133, an e-commerce administrator 135, a machine learning entity 170, an e-commerce organization 169, a government entity 171, a law enforcement entity 172, a person of interest 134. Further at least one of: an e-commerce provider 132, an e-commerce consumer 133, an e-commerce administrator 135, a machine learning entity 170, a government entity 171, a law enforcement entity 172, a person of interest 134 may at least one of: a transfer, an exchange, a buy, a sell at least one of: a dental image 108, dental image dataset 209, an e-commerce dataset 220, a person of interest 134 dataset, landmark probability maps 226, an e-commerce consumer dataset 230, a correlation dataset 331, an object classification dataset 340, a cluster dataset 360, an insurance dataset 410, a provider dataset 440, a bioinformatics dataset 420, a correlated object tracked information dataset 1230 over a communication network, wherein a communication network includes at least one of: a secure communication network, an encrypted communication network, internet, an intranet, an extranet, an internet, an internet transaction service, an online transaction service, a mobile network, a wireless network, an online transaction processing (OLTP) service, an online analytical processing (OLAP) service, a transaction platform.

In an example scenario, the e-commerce processing function 1310, which includes an e-commerce transaction, may at least one of: an exchange, a transfer, a buy, a sell at least one of: a dental image 108, a dental image landmark probabilities, a image class landmark probabilities, object class landmark probabilities, a spatial landmark probability relationships, an object probability landmarks, an object probability relationships, a dental image landmark probability maps over a communication network 110. An e-commerce transaction includes at least one of: business to business (B2B), business to consumer (B2C), consumer to business (C2B), consumer to consumer (C2C), business to administration (B2A) and consumer to administration (C2A). The e-commerce processing function 1310 may further received and/or transmit with at least one of: an e-commerce provider 132, an e-commerce consumer 133, an e-commerce administrator 135, a machine learning entity 170, an e-commerce organization 169, a government entity, a law enforcement entity, a person of interest 134. The e-commerce processing function 1310 may process a transaction of at least one of: a dental image, an e-commerce consumer dental image, dental image dataset, an e-commerce consumer dataset, an e-commerce dataset, a person of interest 134 dataset with at least one of: an e-commerce provider 172, an e-commerce consumer 133, an e-commerce administrator 135, a machine learning entity 170, an e-commerce organization 169, a government entity 171, a law enforcement entity 172, a person of interest 134. Wherein, a transaction includes at least one of: business to business (B2B), business to consumer (B2C), consumer to business (C2B), consumer to consumer (C2C), business to administration (B2A), a consumer to administration (C2A) transactions. At e-commerce processing function 1310 at least one of: a business, consumer, an administrator, a machine learning entity, an e-commerce organization 169, a government entity, a law enforcement entity, a person of interest 134 may process a transaction of at least one of: an exchange, a transfer, a buy, a sell of at least one of: a dental image, a data over a communication network wherein a communication network is at least one of: a secure communication network, an encrypted communication network, the internet, an intranet, an extranet, an internet, an internet transaction service, an online transaction service, a mobile network, a wireless network, an online transaction processing (OLTP) service, an online analytical processing (OLAP) service, a transaction platform.

Figure 14:
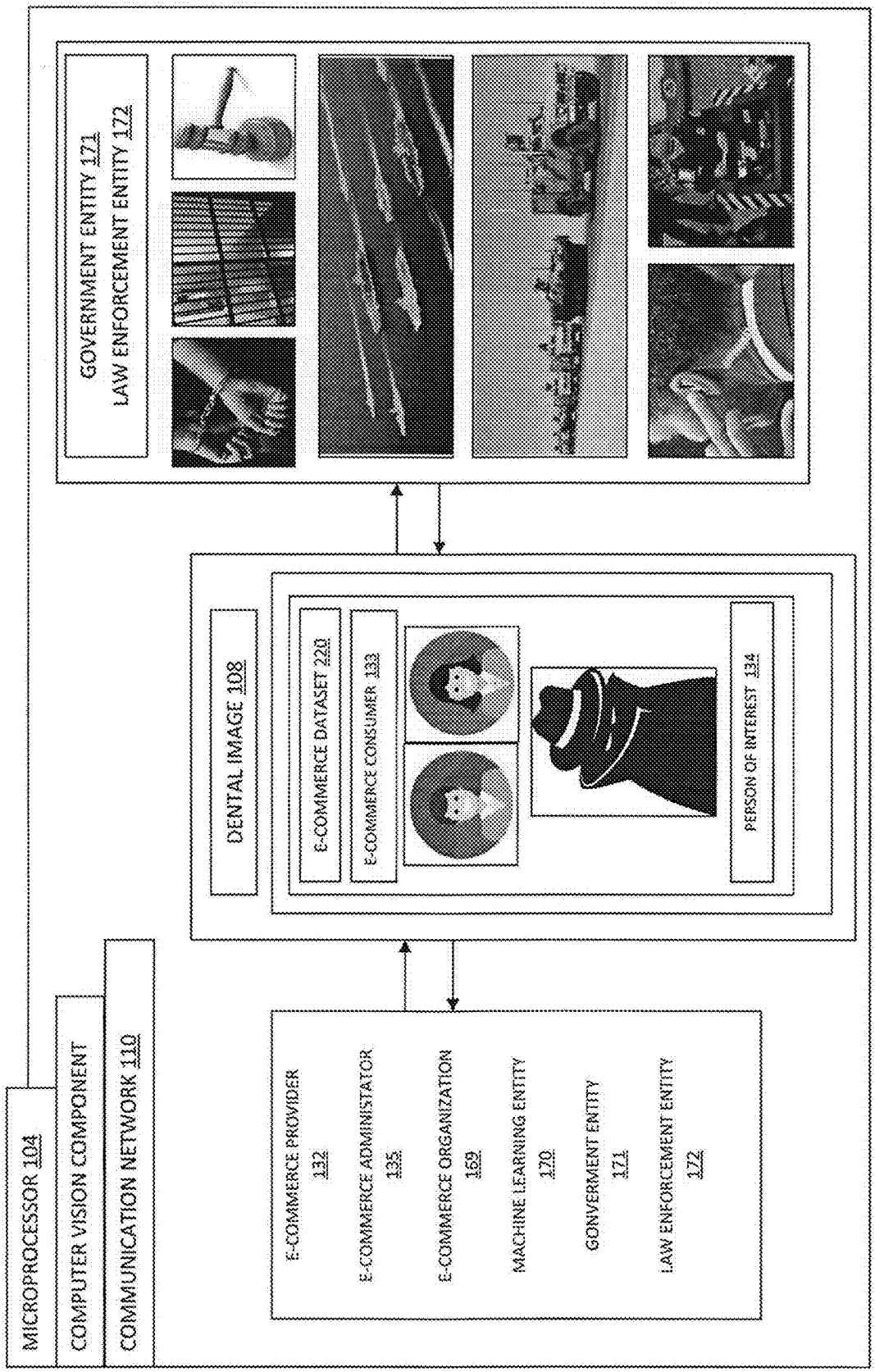
FIG. 14 shows a display diagram illustrating a microprocessor using a computer vision component to provide at least one of: a dental image, a dataset from at least one of: e-commerce consumer, a person of interest over a communication network between various providers, government entities and law enforcement entities according to an embodiment of the invention.

FIG. 14 shows a display diagram illustrating at least one of: a deep learning mechanism 215, a machine learning mechanism 216 that uses a microprocessor 104 that utilizes a computer vision component to transfer dental images and datasets over a communication network. The microprocessor 104 may process the dental images 108 and data with at least one of: a microprocessor 104, an aggregator 106, a processing device, a processor. The microprocessor 106 may process and exchange the dental images 108 and an e-commerce dataset 220 from an e-commerce consumer and/or a person of interest 134 with at least one of: a government entity 171, a law enforcement entity 172 and at least one of: an e-commerce provider 132, an e-commerce consumer 133, an e-commerce administrator 135, machine learning entity 170, an e-commerce organization 169, a government entity 171, a law enforcement entity 172, a person of interest 134.

Further, process 1400 may also use at least one of: a deep learning mechanism 215, a machine learning mechanism 216 that uses a processor that utilizes a computer vision component to transfer dental images 108 and datasets over a communication network. The processor may process and exchange a dental image 108 and an e-commerce dataset 220 to and from at least one of: an e-commerce provider 132, an e-commerce consumer 133, an e-commerce administrator 135, machine learning entity 170, an e-commerce organization 169, a government entity 171, a law enforcement entity 172, a person of interest 134 to at least one of: an e-commerce provider 132, an e-commerce consumer 133, an e-commerce administrator 135, machine learning entity 170, an e-commerce organization 169, a government entity 171, a law enforcement entity 172, a person of interest 134.

Figure 15:
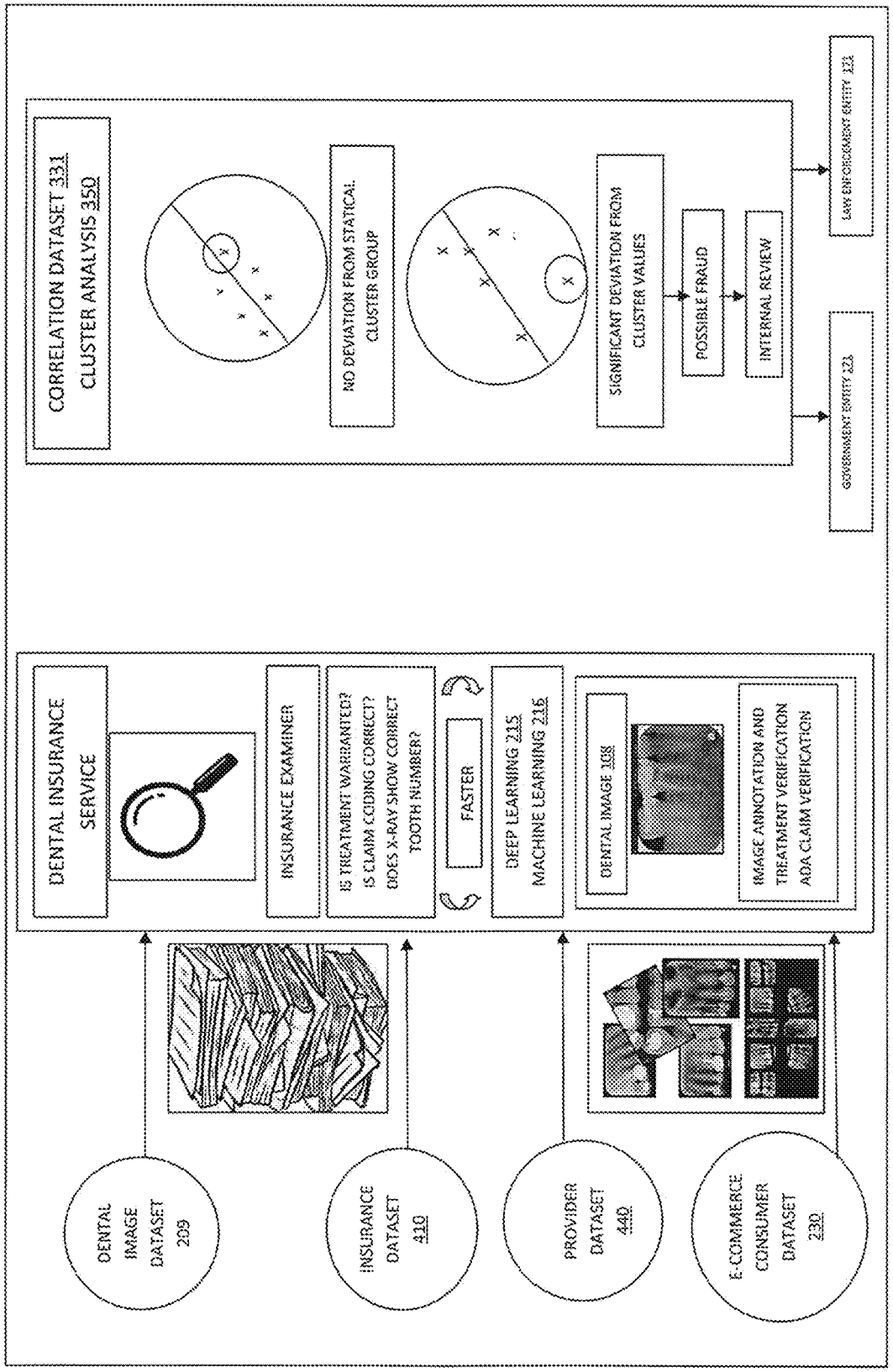
FIG. 15 shows a display diagram illustrating at least one of: a deep learning mechanism, a machine learning mechanism to detect possible insurance fraud according to an embodiment of the invention.

FIG. 15 can be used as an example of processing a dataset with cluster analysis 350 with at least one of: deep learning, machine learning for at least one of: an insurance service, dental insurance service. A dental insurance service and/or an insurance service may include at least one of: an insurance company, an insurance entity, a claims data warehouse. A microprocessor may be configured to receive at least one of: a dental image dataset 209, an insurance dataset 410, a provider dataset 440, an e-commerce dataset 230 and correlate to at least one of: a tooth number, an American Dental Association (ADA) code, an insurance code, a date, an insurance claim data, a claim identifier, a claim number, a duplicate claim associated with the claim identifier, a provider national identification number, a provider's state license number, a license, a provider identification number to an insurance claim dataset. The correlation of the dataset may occur with deep learning and/or machine learning. Process 1500 may use a cluster analysis 350 to produce a correlation dataset 331 and provide to at least one of: an insurance company, a business, an e-commerce provider, an e-commerce consumer, an e-commerce administrator, a machine learning entity 170, an e-commerce organization 169, a national security organization, a judiciary agency, a military agency, a government agency, a government, a law enforcement agency, a microprocessor, a processing device, a processor.

Further, the microprocessor may at least one of: match and identify an insurance dataset to a dental image, verify tooth numbers and provide to an insurance dataset, verify an insurance code and provide to an insurance dataset, alert discrepancies in an insurance dataset and provide an insurance dataset to at least one of: an insurance company, an insurance entity, a claims data warehouse, a business, an e-commerce provider 132, an e-commerce consumer 133, an e-commerce administrator 135, a machine learning entity 170, an e-commerce organization 169, a national security organization, a judiciary agency, a military agency, a government agency, a government, a law enforcement agency, a microprocessor, a aggregator, a processing device, a processor.

At least one of: a microprocessor, a processing device, an aggregator 106, a processor may also identify discrepancy(s) between dental insurance claim(s) by analyzing and comparing attributes of the correlated dental images of an e-commerce consumer 133, a person of interest 134 and an e-commerce dataset 220 with elements of the insurance dataset 410 including at least one of: American Dental Association (ADA) code(s), an insurance code, a date, an insurance claim data, a claim identifier, a claim number, multiple or duplicate claims (instead of a single claim), a national provider identification number for provider/institution(s), a provider's state license number, a license, among others. Corrective action to merge the discrepancy(s) may be implemented automatically to remove the discrepancy(s) between the correlated dental images for at least one of: an e-commerce consumer 133, a person of interest 134, the e-commerce dataset 220, an insurance claim from the insurance dataset 410. Alternatively, corrective action may be implemented manually based on at least one of: feedback, input from at least one of: an e-commerce provider 132, e-commerce consumer 133, e-commerce administrator 135, a machine learning entity 170, an e-commerce organization 169, a government entity, a law enforcement entity, a person of interest 134 associated with an aggregator 106 regarding the discrepancy(s).

At least one of: a microprocessor, an aggregator, a processor, a processing device is configured to match and identify at least one of: a dental image 108, a dataset with all fields of dentistry including: restorative, prosthodontics, periodontics, endodontics, oral surgery, pediodontics, radiology, pathology, tempro-mandibular joint (TMJ) specialist, orthodontist. This matched and identified information may be provided to an e-commerce consumer information dataset 220.

The example scenarios and schemas in FIGS. 1 through 15 are shown with specific components, data types, and configurations. Embodiments are not limited to systems according to these example configurations. At least one of: deep learning, machine learning of dental images for national security utilizing e-commerce may be implemented in configurations employing fewer or additional components in applications and user interfaces. Furthermore, the example schema and components shown in FIGS. 1 through 15 and their subcomponents may be implemented in a similar manner with other values using the principles described herein.

When introducing elements of the present disclosure or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

The present description and claims may make use of the terms "at least one of", "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Although this invention has been described with a certain degree of particularity, it is to be understood that the present disclosure has been made only by way of illustration and that numerous changes in the details of construction and arrangement of parts may be resorted to without departing from the spirit and the scope of the invention.

The invention claimed is:

1. A system for at least one of: a deep learning, a machine learning of a dental image for at least one of: e-commerce, national security the system comprising: a microprocessor, wherein the microprocessor is configured to:
   receive a dental image from at least one of: an e-commerce provider, a business, an e-commerce consumer, an individual, an e-commerce administrator, a machine learning entity, an e-commerce organization, a government entity, a law enforcement entity, a person of interest;
   wherein a person of interest may be at least one of: a terrorist, a violent criminal, a nonviolent criminal, a cybercrime criminal, a political criminal, a white collar criminal, an innocent person;
   the microprocessor may be configured to execute an instruction in any order;
   wherein an instruction is at least one of: a process, a match, an identify, a generate, a train, a provide, a transaction, an exchange, a transfer, a buy, a sell;
   train a microprocessor to process a first dental image with a deep neural network at a first resolution and provide to a dental image dataset;
   match and identify a plurality of dental image landmark probabilities of a first dental image at a first resolution with at least one of: a deep learning, a machine learning to a dental image landmark probabilities dataset and provide to a dental image dataset;
   match and identify image class landmark probabilities of a first dental image at a first resolution with at least one of: a deep learning, a machine learning to an image class landmark probabilities dataset and provide to a dental image dataset;
   match and identify object class landmark probabilities of a first dental image at a first resolution with at least one of: a deep learning, a machine learning to an object class landmark probabilities dataset and provide to a dental image dataset;
   match and identify spatial landmark probability relationships of a first dental image at a first resolution with at least one of: a deep learning, a machine learning to a spatial landmark probability relationships dataset and provide to a dental image dataset;
   match and identify object probability landmarks of a first dental image at a first resolution with at least one of: a deep learning, a machine learning to an object probability landmarks dataset and provide to a dental image dataset;
   match and identify object probability relationships of an dental image at a first resolution with at least one of: a deep learning, a machine learning to an object probability relationships dataset and provide to a dental image dataset;
   generate with at least one of: a deep learning, a machine learning a dental image landmark probability map of a first dental image at a first resolution and provide to a dental image dataset;
   match and identify a dental image landmark probability map of a first dental image at a first resolution with at least one of: a deep learning, a machine learning to a dental image landmark probability map dataset and provide to a dental image dataset;
   train a microprocessor to process a second dental image with a deep neural network at a second resolution and provide to a dental image dataset;
   match and identify a plurality of dental image landmark probabilities of a second dental image at a second resolution with at least one of: a deep learning, a machine learning to a dental image landmark probabilities dataset and provide to a dental image dataset;
   match and identify image class landmark probabilities of a second dental image at a second resolution with at least one of: a deep learning, a machine learning to an image class landmark probabilities dataset and provide to a dental image dataset;
   match and identify object class landmark probabilities of a second dental image at a second resolution with at least one of: a deep learning, a machine learning to an object class landmark probabilities dataset and provide to a dental image dataset;
   match and identify spatial landmark probability relationships of a second dental image at a second resolution with at least one of: a deep learning, a machine learning to a spatial landmark probability relationships dataset and provide to a dental image dataset;
   match and identify object probability landmarks of a second dental image at a second resolution with at least one of: a deep learning, a machine learning to an object probability landmarks dataset and provide to a dental image dataset;
   match and identify object probability relationships of a second dental image at a second resolution with at least one of: a deep learning, a machine learning to an object probability relationships dataset and provide to a dental image dataset;
   generate with at least one of: a deep learning, a machine learning a dental image landmark probability map of a second dental image at a second resolution dataset and provide to a dental image dataset;
   match and identify a dental image landmark probability map of a second dental image at a second resolution with at least one of: a deep learning, a machine learning to a dental image landmark probability map dataset and provide to a dental image dataset;
   train a microprocessor to process a first dental image and a second dental image to a large dataset;
   merge the first dental image and second dental image into a multiple dental image dataset;
   train a microprocessor to process a multiple dental image dataset with a deep neural network with multiple resolutions and provide to a dental image dataset;
   match and identify a plurality of dental image landmark probabilities of a multiple dental image dataset at multiple resolutions with at least one of: a deep learning, a machine learning to a dental image landmark probabilities dataset and provide to a dental image dataset;

match and identify image class landmark probabilities of a multiple dental image dataset at multiple resolutions with at least one of: a deep learning, a machine learning to an image class landmark probabilities dataset and provide to a dental image dataset;
match and identify object class landmark probabilities of a multiple dental image dataset at multiple resolutions with at least one of: a deep learning, a machine learning to an object class landmark probabilities dataset and provide to a dental image dataset;
match and identify spatial landmark probability relationships of a multiple dental image dataset at multiple resolutions with at least one of: a deep learning, a machine learning to a spatial landmark probability relationships dataset and provide to a dental image dataset;
match and identify object probability landmarks of a multiple dental image dataset at multiple resolutions with at least one of: a deep learning, a machine learning to an object probability landmarks dataset and provide to a dental image dataset;
match and identify object probability relationships of a multiple dental image dataset at multiple resolutions with at least one of: a deep learning, a machine learning to an object probability relationships dataset and provide to a dental image dataset;
generate with at least one of: a deep learning, a machine learning a dental image landmark probability map of a multiple dental image dataset with multiple resolutions and provide to a dental image dataset;
match and identify a dental image landmark probability map of a multiple dental image dataset at multiple resolutions with at least one of: a deep learning, a machine learning to a dental image landmark probability map dataset and provide to a dental image dataset;
correlate a dental image dataset with an e-commerce consumer dataset to produce an e-commerce dataset;
wherein an e-commerce consumer dataset includes at least one of: an age, a first name, a gender, a middle initial, a middle name, a last name, a sex, a date of birth, a zip code, an address, a geographic location, a cell phone number, a telephone number, a current medication, a previous medication, a social security number, a marital status, an insurance, an insurance identification number, an email address, an internet protocol address, a change of insurance, an employer, a change of employment, a change of zip code, a change of the previous medication, a change of a marital status, a change of gender, a location, a Global Position System (GPS) location, a Global Navigation System (GLONASS) location, a change of location, a passport activity, a visa status, an immigration data, a biometric measurement, an infection status, a disease status, a contact tracing location, a genetic dataset, an internet browsing history, an e-commerce consumer data;
correlate an e-commerce dataset with at least one of: a terrorist dataset, a suspected terrorist dataset, a violent criminal dataset, a nonviolent criminal dataset, a cybercrime criminal dataset, a political criminal dataset, a white collar criminal dataset, a dataset to produce a person of interest dataset;
process a transaction from at least one of: an e-commerce provider, a business, e-commerce consumer, an individual, an e-commerce administrator, a machine learning entity, an e-commerce organization, a government entity, a law enforcement entity, a person of interest of at least one of: an exchange, a transfer, a buy, a sell of at least one of: a dental image, an e-commerce consumer dental image, a dental image dataset, an e-commerce consumer dataset, an e-commerce dataset, a person of interest dataset over a communication network; wherein a communication network includes at least one of: a secure communication network, an encrypted communication network, the internet, an intranet, an extranet, an internet, an internet transaction service, an online transaction service, a cell phone, a mobile network, a wireless network, an online transaction processing (OLTP) service, an online analytical processing (OLAP) service, a transaction platform to at least one of: an e-commerce provider, a business, an e-commerce consumer, an individual, an e-commerce administrator, a machine learning entity, an e-commerce organization, a national security organization, a judiciary agency, a military agency, a government agency, a government, a law enforcement agency.

2. The microprocessor of claim 1, wherein the microprocessor is configured to process a transaction of at least one of: a dental image, a dental image dataset, an e-commerce consumer dataset, an e-commerce dataset, a person of interest dataset from at least one of: an e-commerce provider, a business, an e-commerce consumer, an individual, an e-commerce administrator, a machine learning entity, an e-commerce organization, a person of interest, a national security organization, a judiciary agency, a military agency, a government agency, a government, a law enforcement agency;
wherein a transaction includes at least one of: business to business (B2B), business to consumer (B2C), consumer to business (C2B), consumer to consumer (C2C), business to administration (B2A), consumer to administration (C2A) transaction.

3. The microprocessor of claim 1, wherein the dental image is obtained from at least one of: a digital x-ray, an x-ray, a digital image, an image, a cell phone, a cell phone captured image, a photographic image, a toothbrush with an imaging device, a toothbrush with an imaging device being a camera, a film based x-ray, a digitally scanned x-ray, a digitally captured x-ray, a scintillator technology based image, a trans-illumination image, a fluorescence technology based image, a blue fluorescence technology based image, a laser based technology based image, a magnetic resonance image (MRI), a computed tomography (CT) scan based image, a cone beam computed tomography (CBCT) image, an image obtained from a wavelength between 1 picometer and 100000 kilometers, a gamma ray based technology, an ultraviolet based technology, a visible light based technology, an infrared based technology, a high frequency based technology, a microwave based technology, a low frequency based technology, a radio wave based technology;

wherein at least one of: an e-commerce provider, a business, an e-commerce consumer, an individual, an e-commerce administrator, a machine learning entity, an e-commerce organization, a person of interest, a national security organization, a judiciary agency, a military agency, a government agency, a government, a law enforcement agency utilizes at least one of: an image capture device, a data storage device;
   wherein at least one of: an image capture device, a data storage device includes one or more of: an x-ray equipment, a digital camera, a cell phone camera, a scintillator counter, an indirect or direct flat panel detector (FPD), a charged couple device (CCD), a phosphor plate radiography device, a picture archiving and communication system (PACS), a photo-stimulable phosphor (PSP) device, a wireless complementary metal-oxide-semiconductor (CMOS) device, an imaging device.

4. The microprocessor of claim 1, wherein the person of interest dataset is configured for storage on at least one of: a processing device, a computing device, a government computing platform, a law enforcement computing platform;
   wherein, the person of interest dataset is configured for secure access by an encrypted security system;
   wherein, the microprocessor is configured for at least one of: a unidirectional, a bidirectional exchange of a person of interest dataset with at least one of: a processing device, an aggregator, a processor, a computing device, a government computing platform, a law enforcement platform;
   wherein, at least one of: an association, a correlation of at least one of: a dental image, an e-commerce consumer dataset of at least one of: an e-commerce consumer, an individual, a person of interest with a bioinformatics dataset may include at least one of: an infection status, a disease status, a contact tracing location may be correlated to at least one of: a geographic location, a Global Position System (GPS), a Global Navigation System (GLONASS) and may be provide over a communication network to at least one of: an insurance company, a business, an e-commerce provider, a business, an e-commerce consumer, an individual, an e-commerce administrator, a machine learning entity, an e-commerce organization, a national security organization, a judiciary agency, a military agency, a government agency, a government, a law enforcement agency, a microprocessor, an aggregator, a processor, a processing device.

5. The microprocessor of claim 1, wherein at least one of: a deep learning, a machine learning of a dental image for e-commerce includes processing the dental image with at least one of:
   a machine learning process, a deep learning process, a computer vision component, a sliding window component, a multiple grid component, a bounding box component, an image classification component configured to generate a dental image confidence score, an object classification component configured to generate a dental object confidence score, a value mechanism component configured to generate a treatment confidence score, a value mechanism component configured to generate a dental product confidence score, a value mechanism component configured to generate a real time dental treatment recommendation, a value mechanism component configured to generate a real time dental product recommendation, a semantic segmentation component configured to generate a semantic segmentation, an instance segmentation component configured to generate an instance segmentation, a supervised learning component configured to annotate, an unsupervised learning component configured to annotate, a recurrent neural network component (RNN) configured to analyze a dataset, an independent neural network component (INDRNN) configured to analyze a dataset, a deep forest decision tree configured to analyze a dataset, a processor configured for a system of memory of dataset, a processor configured for an artificial intelligence system with memory, a processor configured for a system of reactive memory, a processor configured for a system of non reactive memory, a processor configured for a system of rewards training, a processor configured for a system of transfer learning, a processor configured with an object tracking mechanism configured to track object, a processor configured for natural language processing (NLP), a processor configured to use non-linear regression, an image pyramid, a processor configured to use exponential powers laws, a processor configured to use a geometric series, a processor configured to use a binomial distribution;
   a processor configured to exchange at least one of: a dental image, an e-commerce consumer dental image, a dental image dataset, an e-commerce consumer dataset, an e-commerce dataset, a person of interest dataset with a mobile device;
   a processor configured to exchange at least one of: a dental image, an e-commerce consumer dental image, a dental image dataset, an e-commerce consumer dataset, an e-commerce dataset, a person of interest dataset with a cell phone;
   a processor configured for an e-commerce consumer to store at least one of: a dental image, a dental image dataset, an e-commerce consumer dataset, an e-commerce dataset on at least one of: a server, a desktop computer, a workstation, a laptop computer, a cell phone, a tablet, a mobile device, a cloud based storage service;
   a processor configured for an e-commerce consumer to process a transaction of at least one of: an exchange, a transfer, a buy, a sell of at least one of: a dental image, a dataset with at least one of: an e-commerce consumer, an individual, an e-commerce provider, a business, an e-commerce administrator, a machine learning entity, an e-commerce organization, a government entity, a law enforcement entity, a person of interest in exchange for at least one of: a currency, a data, a discount, a product, a good, a software, an application, an advertisement.

6. The microprocessor of claim 1, wherein the training of a first dental image with a deep neural network occurs concurrently with learning a plurality of dental image landmark probability maps;
   wherein the training of a second dental image with a deep neural network occurs concurrently with learning a plurality of dental image landmark probability maps;
   wherein the training of a multiple dental image dataset with a deep neural network occurs concurrently with learning a plurality of dental image landmark probability maps.

7. The microprocessor of claim 1, wherein at least one of: a dental image, a dataset is configured to compensate for at least one of: a distorted information, a missing image information;

wherein a microprocessor is configured to alert a change in the dental object tracking mechanism;

wherein the microprocessor is configured to execute an instruction in any order;

wherein the microprocessor is configured to omit an instruction in any order;

wherein an instruction is at least one of: a process, a match, an identify, a generate, a train, a provide, a transaction, an exchange, a transfer, a buy, a sell.

8. The microprocessor of claim 1, wherein the dental image is processed with at least one convolutional neural network layer configured to extract at least one of: a dental image landmark probabilities, an image class landmark probabilities, an object class landmark probabilities, a spatial landmark probability relationships, an object probability landmarks, an object probability relationships, a dental image landmark probability map, a person of interest dataset, a data.

9. The microprocessor of claim 1, wherein the microprocessor is further configured to:

receive at least one of: a dental image, an e-commerce consumer dental image, a dental image dataset, an e-commerce consumer dataset, an e-commerce dataset, a person of interest dataset and correlate to at least one of: a tooth number, an American Dental Association (ADA) code, an insurance code, a date, an insurance claim data, a claim identifier, a claim number, a duplicate claim associated with the claim identifier, a provider national identification number, a provider's state license number, a license, a provider identification number to an insurance dataset, a data and provide to an insurance dataset;

verify a dental image and provide to an insurance dataset;

verify a tooth number and provide to an insurance dataset;

verify an insurance code and provide to an insurance dataset;

alert a discrepancy in an insurance dataset;

provide an insurance dataset to at least one of: an insurance company, a business, an e-commerce provider, a business, an e-commerce consumer, an individual, an e-commerce administrator, a machine learning entity, an e-commerce organization, a national security organization, a judiciary agency, a military agency, a government agency, a government, a law enforcement agency, a processing device.

10. The microprocessor of claim 1, further correlating at least one of: a dental image dataset, an e-commerce consumer dataset, an e-commerce dataset and at least one of: a dental image, a dental image landmark with a genetic dataset to generate a genetic connection;

where in a genetic dataset includes at least one of: a node, a genotype, a gene identifier, a gene sequence, a single nucleotide polymorphism, a nucleic acid sequence, a protein sequence, an annotating genome, a shotgun sequence, a periodontal disease, a caries susceptibility, a malocclusion, a pathology, an impacted tooth, a tooth loss, an angle's classification of malocclusion, a diabetes diagnosis, a medical condition;

determining a weight associated genetic connection between two directly connected nodes;

determine the shortest genetic connection path;

determining a weight associated with each genetic connection between two directly connected nodes;

provide to at least one of: an e-commerce provider, a business, an e-commerce consumer, an individual, an e-commerce administrator, a machine learning entity, an e-commerce organization, a national security organization, a judiciary agency, a military agency, a government agency, a government, a law enforcement agency.

11. The microprocessor of claim 1, wherein the e-commerce dataset is configured to produce:

a person of interest location of at least one of: a terrorist, a violent criminal, a nonviolent criminal, a cybercrime criminal, a political criminal, a white collar criminal, an innocent person, an e-commerce consumer;

provide a person of interest location to at least one of: a national security organization, a judiciary agency, a military agency, a government agency, a government, a law enforcement agency, an e-commerce consumer, an individual, an e-commerce provider, a business, an e-commerce administrator, a machine learning entity, an e-commerce organization to a client device, wherein a client device includes at least one of: a server, a desktop computer, a workstation, a laptop computer, a cell phone, a tablet, a mobile device, a cloud based storage service, a processing device.

12. The microprocessor of claim 1, wherein the microprocessor is configured to provide at least one of: a person of interest location aid, a dental object tracking mechanism, a dental image probability diagnosis to at least one of: a national security organization, a judiciary agency, a military agency, a government agency, a government, a law enforcement agency, an e-commerce consumer, an individual, an e-commerce provider, a business, an e-commerce administrator, a machine learning entity, an e-commerce organization.

13. A microprocessor for providing at least one of: a deep learning, a machine learning of a dental image for at least one of: e-commerce, national security the method comprising:

a computer vision component configured to analyze the dental image;

a memory configured to store instructions associated with at least one of: a microprocessor, a processing service;

at least one of: a microprocessor, a processing service coupled to the computer vision component and the memory using at least one of: a microprocessor, processing service executing the instructions associated with an aggregator, wherein the aggregator includes:

an image processing engine configured to:

receive a dental image from at least one of: an e-commerce provider, a business, an e-commerce consumer, an individual, an e-commerce administrator, a machine learning entity, an e-commerce organization, a government entity, a law enforcement entity, a person of interest;

wherein a person of interest is at least one of: a terrorist, a violent criminal, a nonviolent criminal, a cybercrime criminal, a political criminal, a white collar criminal, an innocent person;

the microprocessor may be configured to execute an instruction in any order;

wherein an instruction is at least one of: a process, a match, an identify, a provide, a transaction, an exchange, a transfer, a buy, a sell;

match and identify a first dental image at a first resolution to at least one of: a dental image landmark probabilities dataset, an image class landmark probabilities dataset, an object class landmark probabilities dataset, a spatial landmark probability relationships dataset, an object probability landmarks dataset, an object probability relationships dataset, a dental image landmark probability map, a dental image landmark probability map dataset and provide to a dental image dataset;

match and identify a second dental image at a second resolution to at least one of: a dental image landmark probabilities dataset, an image class landmark probabilities dataset, an object class landmark probabilities dataset, a spatial landmark probability relationships dataset, an object probability landmarks dataset, an object probability relationships dataset, a dental image landmark probability map, a dental image landmark probability map dataset and provide to a dental image dataset;

merge the first dental image and second dental image into a multiple dental image dataset;

match and identify a multiple dental image dataset at a multiple resolution to at least one of: a dental image landmark probabilities dataset, an image class landmark probabilities dataset, an object class landmark probabilities dataset, a spatial landmark probability relationships dataset, an object probability landmarks dataset, an object probability relationships dataset, a dental image landmark probability map, a dental image landmark probability map dataset and provide to a dental image dataset;

correlate a dental image dataset with an e-commerce consumer dataset to produce an e-commerce dataset;

wherein an e-commerce consumer dataset includes at least one of: an age, a first name, a gender, a middle initial, a middle name, a last name, a sex, a date of birth, a zip code, an address, a geographic location, a cell phone number, a telephone number, a current medication, a previous medication, a social security number, a marital status, an insurance, an insurance identification number, an email address, an internet protocol address, a change of insurance, an employer, a change of employment, a change of zip code, a change of the previous medication, a change of a marital status, a change of gender, a location, a Global Position System (GPS) location, a Global Navigation System (GLONASS) location, a change of location, a passport activity, a visa status, an immigration data, a biometric measurement, an infection status, a disease status, a contact tracing location, a genetic dataset, an internet browsing history, an e-commerce consumer data;

correlate an e-commerce dataset with at least one of: a terrorist dataset, a suspected terrorist dataset, a violent criminal dataset, a nonviolent criminal dataset, a cybercrime criminal dataset, a political criminal dataset, a white collar criminal dataset to produce a person of interest dataset;

process a transaction from at least one of: an e-commerce provider, a business, an e-commerce consumer, an individual, an e-commerce administrator, a machine learning entity, an e-commerce organization, a government entity, a law enforcement entity, a person of interest of at least one of: an exchange, a transfer, a buy, a sell of at least one of: a dental image, a dental image dataset, an e-commerce consumer dataset, an e-commerce dataset, a person of interest dataset over a communication network to at least one of: an e-commerce provider, a business, an e-commerce consumer, an individual, an e-commerce administrator, a machine learning entity, an e-commerce organization, a national security organization, a judiciary agency, a military agency, a government agency, a government, a law enforcement agency, a microprocessor, a processor, a processing device;

wherein a communication network includes at least one of: a secure communication network, an encrypted communication network, the internet, an intranet, an extranet, an internet, an internet transaction service, an online transaction service, a cell phone, a mobile network, a wireless network, an online transaction processing (OLTP) service, an online analytical processing (OLAP) service, a transaction platform.

14. The microprocessor of claim 13, wherein the e-commerce provider includes at least one of: a business, a business entity, a business owner, an employer, a wholesaler, a retailer, a professional, a dentist, a dental hygienist, a physician, a health professional, a veterinarian, a veterinarian professional, a dental professional, a health professional, a group, a research entity, a law enforcement entity, a public administration entity, a government agency, a government, a bioinformatics service, an insurance company, a cloud based storage service;

wherein an e-commerce consumer includes at least one of: an individual, a guardian, a group, an employee, a person of interest;

wherein an e-commerce administrator includes at least one of: an administrator, an administrator entity, a government agency, a government;

wherein, at least one of: an insurance company, a business, an e-commerce provider, an e-commerce consumer, an individual, an e-commerce administrator, a machine learning entity, an e-commerce organization, a national security organization, a judiciary agency, a military agency, a government agency, a government, a law enforcement agency may track at least of: a e-commerce consumer, a person of interest based on at least one of: a Global Position System (GPS), a Global Navigation System (GLONASS), a location with at least one of: a dental image, an e-commerce dataset.

15. The microprocessor of claim 13, wherein the e-commerce consumer dataset is provided to an e-commerce provider upon at least one process to:

verify a compliance of at least one of: a dental image, a bioinformatics dataset, an e-commerce consumer dataset with a regulatory policy;

verify an authorization by the e-commerce consumer to analyze at least one of: a dental image, a bioinformatics dataset, an e-commerce consumer dataset;

authenticate at least one of: an e-commerce consumer, an individual, a person of interest to process a transaction of at least one of: an exchange, a transfer, a buy, a sell of an e-commerce dataset with at least one of: an e-commerce consumer, an individual, an e-commerce provider, a business, an e-commerce administrator, a machine learning entity, an e-commerce organization, a national security organization, a judiciary agency, a military agency, a government agency, a government, a law enforcement agency in exchange for at least one of: a currency, a data, a discount, a product, a good, a software, an application, an advertisement.

16. The microprocessor of claim 13, wherein the e-commerce organization includes at least one of: an insurance service, a dental insurance service and wherein at least one of: an insurance service, a dental insurance service provides an insurance dataset including at least one of: an American dental association (ADA) code, a date, a claim identifier, a claim number, a duplicate claim associated with the claim identifier, a provider national identification number, a provider's state license number, a license, a provider identification number, a data;

wherein the insurance dataset may be at least one of: analyzed, integrated, correlated to least one of: a dental image, a dental image landmark, an individual information dataset, an e-commerce dataset, a person of interest dataset and may be provided to at least one of: an insurance company, an e-commerce provider, a business, an e-commerce consumer, an individual, an e-commerce administrator, a machine learning entity, an e-commerce organization, a government entity, a law enforcement entity.

17. The microprocessor of claim 13, wherein the e-commerce organization includes a bioinformatics service; wherein the bioinformatics service provides a bioinformatics dataset including at least one of: a node, a genotype, a gene identifier, a gene sequence, a single nucleotide polymorphism, a nucleic acid sequence, a protein sequence, an annotating genome, a shotgun sequence, a periodontal disease, a caries susceptibility, a malocclusion, a pathology, an impacted tooth, a tooth loss, an angle's classification of malocclusion, a diabetes diagnosis, a medical condition;

wherein, the bioinformatics dataset may be at least one of: analyzed, integrated, correlated to least one of: a dental image, a dental image landmark, a dental image dataset, an individual information dataset, an e-commerce consumer dataset, an e-commerce dataset, a person of interest dataset and may be provided to at least one of: a bioinformatics service, an e-commerce provider, a business, an e-commerce consumer, an individual, an e-commerce administrator, a machine learning entity, an e-commerce organization, a government entity, a law enforcement entity.

18. The e-commerce consumer dataset of claim 13, wherein an e-commerce consumer dataset includes at least one e-commerce consumer data.

19. The method of claim 13, wherein the processor is further configured to:

receive at least one of: a dental image, an e-commerce consumer dental image, a dental image dataset, an e-commerce consumer dataset, an e-commerce dataset, a person of interest dataset and correlate to at least one of: a tooth number, an American Dental Association (ADA) code, an insurance code, a date, an insurance claim data, a claim identifier, a claim number, a duplicate claim associated with the claim identifier, a provider national identification number, a provider's state license number, a license, a provider identification number to an insurance claim dataset, a data and provide to an insurance claim dataset;

verify a dental image and provide to an insurance claim dataset;

verify a tooth a number and provide to an insurance claim dataset;

verify an insurance code and provide to an insurance claim dataset;

alert a discrepancy in an insurance claim dataset;

provide an insurance dataset to at least one of: an insurance company, a business, an e-commerce provider, an e-commerce consumer, an individual, an e-commerce administrator, a machine learning entity, an e-commerce organization, a national security organization, a judiciary agency, a military agency, a government agency, a government, a law enforcement agency, a processing device.

20. A system of at least one of: a deep learning, a machine learning of a dental image based on a genetic sample for at least one of: e-commerce, national security the system comprising: a processor wherein a processor is configured to:

execute an instruction in any order;

match and identify at least one of: a dental anatomy, a dental pathology based on a genetic sample to at least one of: a dental image, an e-commerce dataset;

match and identify a genetic probability based on at least one of: a dental image, an e-commerce dataset;

quantitatively determining a level of RNA transcripts of a gene from at least one of: a tissue, a saliva sample, a sample obtained from at least one of: an e-commerce consumer, an individual, a person of interest and at least one of: associate, correlate it to at least one of: a dental image, an e-commerce dataset;

normalize a level of RNA transcripts of a gene to levels of RNA transcript of at least one reference gene to produce a normalized RNA expression levels and at least one of: associate, correlate it to at least one of: a dental image, an e-commerce dataset;

comparing a normalized RNA expression levels of a gene to a range of normalized RNA expression levels of the same gene obtained from at least one of: a dental anatomy dataset reference dataset, a dental pathology reference set and at least one of: associate, correlate it to at least one of: a dental image, an e-commerce dataset;

predict a risk of a dental pathology of at least one of: an e-commerce consumer, an individual, a person of interest based on the comparison of a normalized RNA expression levels of a gene to a normalized RNA expression levels of a gene and at least one of: associate, correlate it to a dental image and provide to an e-commerce dataset;

the e-commerce dataset may be associated with at least one of: a location, a Global Position System (GPS), a Global Navigation System (GLONASS), a location for at least one of:

tracking a person of interest, a contact tracing location;

provide to at least one of: an e-commerce provider, a business, an e-commerce consumer, an individual, an e-commerce administrator, a machine learning entity, an e-commerce organization, a national security organization, a judiciary agency, a military agency, a government agency, a government, a law enforcement agency, a microprocessor, an aggregator, a processor, a processing device.

* * * * *